US007749751B2

(12) United States Patent
Depicker et al.

(10) Patent No.: US 7,749,751 B2
(45) Date of Patent: Jul. 6, 2010

(54) OPTIMIZED T-DNA TRANSFER AND VECTORS THEREFOR

(75) Inventors: Anna Depicker, Merelbeke (BE); Vladimir Mironov, Ghent (BE); Franky Terras, Ghent (BE); Willem Broekaert, Dilbeek (BE); Sylvie De Buck, Knokke-Heist (BE); Chris De Wilde, Herdersem-Aalst (BE)

(73) Assignee: CropDesign N.V. (BE)

( * ) Notice: Subject to any disclaimer, the term of this patent is extended or adjusted under 35 U.S.C. 154(b) by 1906 days.

(21) Appl. No.: 10/168,072

(22) PCT Filed: Dec. 13, 2000

(86) PCT No.: PCT/EP00/12683

§ 371 (c)(1),
(2), (4) Date: Oct. 29, 2002

(87) PCT Pub. No.: WO01/44482

PCT Pub. Date: Jun. 21, 2001

(65) Prior Publication Data

US 2003/0140376 A1 Jul. 24, 2003
US 2008/0047035 A9 Feb. 21, 2008

Related U.S. Application Data

(60) Provisional application No. 60/195,758, filed on Apr. 10, 2000.

(51) Int. Cl.
*C12N 15/63* (2006.01)
*C12N 15/09* (2006.01)
*C12N 15/00* (2006.01)

(52) U.S. Cl. ............. 435/320.1; 435/468; 435/469; 800/278; 536/23.1; 536/24.2

(58) Field of Classification Search .............. None
See application file for complete search history.

(56) References Cited

U.S. PATENT DOCUMENTS 7,087,812 B1 * 8/2006 Kuraya et al. .......... 800/294

FOREIGN PATENT DOCUMENTS

| EP | 1 136 560 | 9/2001 |
|---|---|---|
| WO | WO 99/01563 | 1/1999 |
| WO | WO99/25855 | * 5/1999 |
| WO | WO 99/25855 | 5/1999 |

OTHER PUBLICATIONS

Wang et al 1987 Mol Gen Genet 210:338-346.*
Gielen, J. et al. (1984) The Complete Nucleodide Sequence of the TL-DNA of the *Agrobacterium tumefaciens* Plasmid PTiAch5. *EMBO Journal* 3 (4) 835-684.
De Buck, Sylvie et al., (1999) "The DNA sequences of T-DNA junctions suggest that complex T-DNA loci are formed by a recombination process resembling T-DNA integration", *The Plant Journal*, 20(3):295-304.
Van Haaren, M.J.J. et al., (1988), "Function of heterologous and pseudo border repeats in T region transfer via the octopine virulence system of *Agrobacterium tumefaciens*", Plant Molecular Biology, 11:773-781.
Hanson, Bill et al., (1999) "A simple method to enrich an *Agrobacterium*-transformed population for plants containing only T_DNA sequences", *The Plant Journal*, 19(6):727-734.
Kononov, Maria E. et al., (1997) "Integration of T-DNA binary vector 'backbone' sequences into the tobacco genome: evidence for multiple complex patterns of integration", *The Plant Journal*, 11(5):945-957.
Peralta, Ernest G. et al., (1986) "Overdrive, a T-DNA transmission enhancer on the *A. tumefaciens* tumour-inducing plasmid", *The EMBO Journal*, vol. 5, No. 6, pp. 1137-1142.
Tinland, Bruno et al., (1995) "The *Agrobacterium tumefaciens* virulence D2 protein is responsible for precise integration of T-DNA into the plant genome", *The EMBO Journal*, vol. 14, No. 14, pp. 3585-3595.
De Buck, Sylvie et al., (2000) "T-DNA vector backbone sequence are frequently integrated into the genome of transgenic plants obtained by *Agrobacterium*-mediated transformation", *Molecular Breeding*, 6:459-468.
Wang, K., et al., "Overexpression of *virD1* and *virD2* Genes in *Agrobacterium tumefaciens* Enhances T-Complex Formation and Plant Transformation", Journal of Bacteriology, vol. 172, No. 8, (1990), pp. 4432-4440.

* cited by examiner

*Primary Examiner*—Anne Marie Grunberg
*Assistant Examiner*—Brent Page
(74) *Attorney, Agent, or Firm*—Connolly Bove Lodge & Hutz LLP

(57) ABSTRACT

The present invention relates to T-DNA vectors and methods for obtaining transgenic eukaryotes using said vectors. The transgenic eukaryotes are characterized in that they contain the T-DNA but not the illegitimately transferred vector backbone sequence. This is achieved by modifying the T-DNA borders such that they are more efficiently nicked or such that they allow elimination of illegitimately transferred vector backbone sequences by means of recombination.

25 Claims, 6 Drawing Sheets

Sizes of LB and RB inner and outer regions (all from pTiAch5; Gielen et al. 1984) in K- and Hsb T-DNA vectors:

K T-DNA vector: LB inner region: 689 bp
  LB outer region: 306 bp
  RB inner region: 251 bp
  RB outer region: 146 bp Hsb T-DNA vector: LB inner region: ~30 bp
  LB outer region: 306 bp
  RB inner region: 49 bp
  RB outer region: 146 bp

US 7,749,751 B2

OPTIMIZED T-DNA TRANSFER AND VECTORS THEREFOR

RELATED APPLICATIONS

This application is a national stage application (under 35 U.S.C. 371) of PCT/EP00/12683, filed Dec. 13, 2000, which claims benefit of U.S. Provisional Application 60/195,758, filed Apr. 10, 2000, and of European application 99879264.1 filed Dec. 16, 1999.

FIELD OF INVENTION

The present invention relates to the field of molecular biology. More particularly, it describes methods for the incorporation of foreign DNA into the genome of eukaryotic cells such as plant cells. The specifics of the current invention lie in the design of the border repeats flanking Agrobacterially transferred T-DNA such that read-through through the left T-DNA border is significantly decreased and/or that integrated vector backbone DNA can easily be removed. Thus, the frequency of obtaining transgenic eukaryotic cells containing only the T-DNA is increased.

BACKGROUND TO THE INVENTION

Improved plant varieties have been obtained by 'classical' crossbreeding ever since man exchanged nomadic existence for permanent settlement. In the more recent history, scientists started to unravel the behavior of genetic material during crossings and plant breeders could, and still do benefit from the knowledge contained within the Mendelian laws predicting the distribution of a given genetic trait in the offspring of a crossing. With the advent of plant molecular biology plant breeders can, with an ever increasing precision, insert novel chimeric genes into the genome of a plant. A variety of techniques is nowadays available to mediate genetic transformation of plants including agrolistics, microinjection, electroporation, direct gene transfer and bombardment with DNA-coated particles. A preferred and widely used plant transformation system makes use of the soil bacterium *Agrobacterium* (Zupan and Zambryski 1995, Gelvin 1998a, Gheysen et al. 1998). Nowadays, *Agrobacterium* is not only used to transform plants but also to transform yeast, moulds and filamentous fungi (Bundock et al. 1995, de Groot et al. 1998, Gouka et al. 1999, WO98/45455). It has furthermore been shown that components of the T-DNA production and transfer machinery of *Agrobacterium* are useful for import of DNA into nuclei of mammalian cells, opening perspectives for use of these components in gene therapy (Ziemienowicz et al. 1999). *Agrobacterium* transfers into a eukaryotic cell nucleus any DNA located on the T-DNA. This T-DNA is part of the wild-type Ti- (in case of *Agrobacterium tumefaciens*) or Ri-plasmid (in case of *A. rhizogenes*). Wild-type T-DNA carries the genes causing, after integration in the plant genome, crown gall tumors or the hairy root syndrome in case of infection with *A. tumefaciens* or *A. rhizogenes*, respectively. Also located on the wild-type Ti- or Ri-plasmids are vir genes (virulence genes) which are activated by plant phenolic compounds. Products of the vir genes are responsible for the transfer of the T-DNA into the eukaryotic genome. For transformation purposes, the T-DNA is disarmed (i.e. all disease-causing genes are removed) and vir genes are supplied either in trans on a helper plasmid (the T-DNA encompassing heterologous gene(s) is then located on a second binary plant transformation vector) or in cis in case of a co-integrate plant transformation vector. The heterologous genes of interest are cloned in between the two T-DNA 22 bp (in case of octopine Ti plasmids) or 25 bp (in case of nopaline Ti plasmids) imperfect border core sequences constituting to the right border (RB) and the left border (LB), that are the only in cis elements necessary to direct T-DNA processing. The border core sequences in RB and LB are organized as imperfect repeats.

The VirD1 and VirD2 proteins produce a single-stranded nick between the third and fourth base in the bottom strand of each border repeat (Yanofsky et al. 1986). Increased levels of VirD1 and VirD2 enhance the production of T-DNA complexes inside *Agrobacterium* and result in an increased plant transformation efficiency (Wang et al. 1990).

For many years, it was believed that only the DNA between the repeats, the T-DNA, and not the vector DNA external to the T-DNA was transferred to the eukaryotic cell. However, recent and more detailed characterization of the DNA inserts in transgenic plants demonstrates that also vector backbone sequences integrate very frequently into the plant genome (Martineau et al. 1994, Ramanathan and Veluthambi 1995, Cluster et al. 1996, van der Graaff et al. 1996, Kononov et al. 1997, Wenck et al. 1997, Wolters et al. 1998).

The authors of the present invention have previously found that the frequency of integration of vector sequences is not influenced by the plant species or the transformation method used. This is consistent with the view that transfer of vector backbone sequences is the consequence of read-through past the LB, a process that is occurring within the *Agrobacterium* cells and is most probably determined by factors within these cells. It should, however, be noticed that others reported vector backbone integration in 33% of *Arabidopsis* transformants obtained via root transformation and in up to 62% of transformants obtained via vacuum infiltration (Wenck et al. 1997). This implies that the transformation method used could be another factor influencing the frequency of vector backbone integration. Integration of vector backbone sequences has been reported to occur in many plant species including Petunia (Virts and Gelvin 1985, Cluster et al. 1996), *Arabidopsis* (Van der Graaff et al. 1996, Wenck et al. 1997), tobacco (Ramanathan and Veluthambi 1995, Kononov et al. 1997, Wenck et al. 1997), and potato (Wolters et al. 1998). Vector backbone integration is apparently independent of the type of *Agrobacterium* strain used for plant transformation (Kononov et al. 1997).

The inventors have previously analyzed different series of transformants for the presence of vector backbone sequences by using specific PCR reactions and DNA gel blot analysis. Three different transformation methods in two different plant species were evaluated, namely *Arabidopsis thaliana* root and leaf transformation and *Nicotiana tabacum* protoplast and leaf transformation. Finally, the influence of the replicon type, the ColE1 and pVS1 replicons, was evaluated. The results showed that neither the plant species nor the explant type used for transformation, the replicon type or the selection have a major influence on the frequency with which integration of vector sequences occurred. In the past, it was postulated that this transfer of vector DNA that does not belong to the T-DNA could be the result of read-through at the left border, which would prevent the normal termination of the T-DNA transfer. Alternatively, DNA transfer could start at the left border and proceed towards the right border (Ramanathan and Veluthambi, 1995; van der Graaff et al., 1996). In the transgenic plants described above, however, it was observed that many contain vector backbone sequences linked to the left border as well as vector junctions with the right T-DNA border. DNA gel blots indicate that in most of these plants the complete vector sequence is integrated. Therefore, it was postulated that integration in the plant genome of complete vector backbone sequences can be the result of a conjugative transfer initiated at the right border and subsequent continued copying at the left and right borders, called read-through. This model implies that the left border is not frequently recognized as an initiation site for DNA transfer and that the right border is not efficiently recognized as a termination site for DNA transfer. These observations comply with the results of previous work showing that the right border region is intrinsically more active than the left border region in promoting T-DNA transformation (Jen and Chilton 1986a, b, Caplan et al. 1985). From all available data, it can be concluded that T-strand formation starts much more frequently at the right border than at the left border region.

In the future, it will be of utmost importance to prevent or to cure vector backbone integration as a consequence of *Agrobacterium*-mediated transformation. Firstly, regulatory authorities are demanding that transgenic plants to be released on the common marketplace are free of vector backbone sequences. Such backbone sequences can carry bacterial origins of replications, bacterial antibiotic resistance genes and possibly a number of other (foreign) genes. The same rigorous concerns will also be expressed by consumers who are becoming increasingly aware of such potential hazards associated with plant biotechnology. Secondly, also from a scientific point of view it is desirable not to have vector backbone integration in the genome of plants. Such sequences can influence transgene expression (Iglesias et al. 1997, Matzke and Matzke 1998, Jakowitsch et al. 1999). Vector backbone integration is also likely to interfere with T-DNA tagging experiments. Tags can be considerably longer than expected (Martineau et al. 1994) and vector backbone integration might also be the explanation for the fact that in a large percentage of T-DNA tagged *Arabidopsis* plants the T-DNA is not co-segregating with a mutant phenotype (Errampali et al. 1991, Feldmann 1991, Koncz et al. 1992, Van Lijsebettens et al. 1991).

Although the phenomenon of occasional vector backbone integration was already encountered as early as 1982 by Ooms et al., it lasted till 1995 for a first solution to be suggested by Ramanathan and Veluthambi (1995): " . . . novel binary vectors with 'stop-transfer' signals adjacent to the left border may be constructed". Since then, one has tried to understand the mechanism of vector backbone integration. A possible reason was discussed by Wenck et al. (1997): " . . . inefficient nicking may be due to low amounts of virulence proteins, primarily VirD2". Only very recently, however, methods were disclosed that prevent read-through at the T-DNA borders (WO99/01563) and by Hanson et al. (1999). These methods are based on including sequences outside the borders. These sequences are either genes coding for toxic compounds or sequences capable of interacting with DNA-binding proteins or sequences that are enriched in G+C nucleotides. A major drawback of the methods described in WO99/01563 and Hanson et al. (1999) is that the regeneration of plant transformants carrying more than the T-DNA region in their genome is prevented. It is conceivable that such methods impair the overall transformation efficiency, i.e. lower numbers of transformants will be obtained from a given transformation experiment. It was indeed reported by Hanson et al. (1999) that tobacco transformation efficiencies drop by as much as 30%. Nevertheless, Hanson et al. (1999) described their approach as a useful tool 'for the elimination of non-T-DNA sequences from transgenic individuals'.

The current invention describes a solution to the technical problem of undesired vector backbone integration and provides advantages over existing methods.

SUMMARY OF THE INVENTION

The invention describes transformation vectors comprising a T-DNA with flanking T-DNA borders. The T-DNA vectors are characterized in that they are modified such that they allow genetic transformation of a eukaryotic cell only with the T-DNA and not with vector backbone sequences. This is accomplished either by preventing transfer of vector backbone sequences to the genome of a eukaryotic cell or by curing of vector backbone sequences transferred to the genome of a eukaryotic cell. Said modified T-DNA vectors allow for an efficient processing of the left border by the nicking complex involving at least VirD1 and VirD2 or allow for excision of transferred vector backbone sequences.

A first embodiment of the invention comprises optimized T-DNA vectors including a modification of the T-DNA right border comprising a single right border core sequence flanked by a right border outer region and/or a modification, including multiplication, of the left T-DNA border designed as:

a) a single left border core sequence flanked by a natural left border outer region and an intra-T-DNA left border proximal region with a length of 10 to 100 bp, preferably 20-100 bp, and which is enriched in the number of A- and T-residues, the percentage of AT-residues preferably being 60 to 85%, more preferably being 64 to 80%, most preferably being 65, 66, 67, 68, 69, 70, 71, 72, 73, 74, 75, 76, 78 or 79%, provided that said intra-T-DNA left border proximal region is not the corresponding natural octopine type left border inner region, or, b) a single left border core sequence flanked only by a natural left border inner region; or, c) a single left border core sequence; or d) a tandem repeat of several left border core sequences flanked only by a natural left border outer region, with the tandem repeat preferably containing 2-3 left border core sequences but not excluding a higher copy number of the left border core imperfect repeat and with said repeated left border core sequences in said tandem being separated by a sequence of at least 10-20 bp optionally carrying stop codons in the three reading frames and in both directions; or e) an integral nopaline-type left border region adjacent to and downstream or upstream of the integral octopine-type left border region.

Another embodiment of the invention comprises optimized T-DNA transformation vectors with additional DNA sequences outside the T-DNA border core repeats enabling post-transformational removal of integrated vector backbone sequences. Said additional DNA sequences modify, including multiply, the T-DNA border regions or parts thereof and comprise:

f) recombination sites organized as repeats downstream of the left border core sequence and upstream of the right border core sequence; or g) said DNA sequences of (f) further modified by adding a second copy of a left border region positioned upstream of and preferably adjacent to the single right border outer region and said recombination site upstream of the core sequence of said second left border region; or h) said recombination sites of (f) with a recombinase gene, downstream of said recombination site downstream of the left border core sequence, and preferably, when present, adjacent to and downstream of the left border outer region; or i) a DNA sequence located downstream of the left border region, said DNA sequence comprising a recombinase gene flanked by repeats of recombination sites as defined in (h) and further comprising a second copy of a left border region downstream of said recombinase; or j) the DNA sequence of (i) with additional recombination sites organized as repeats downstream of the second left border core sequence and upstream of the single right border core sequence;

In any of said modifications (f), (g), (h), (i) or (j), said recombination sites are located adjacent to and downstream and/or upstream of the left- and/or right border core sequences or are separated from the left- and/or right border core sequences by a sequence of at least 10-20 bp in length optionally carrying stop codons in the three reading frames and in both directions.

In any of said modifications (f), (g), (h), (i) or (j), said recombination sites are either site-specific recombination sites arranged as direct repeats or transposon border sequences arranged as inverted repeats and said recombinase gene is either a site-specific recombinase gene or a transposase gene, respectively.

Another embodiment of the invention includes transformation vectors in which any of said modifications as defined in (a) to (j), is applied, or are applied in combination. These transformation vectors comprise vectors used in *Agrobacterium*-mediated transformation including octopine-type binary transformation vectors, nopaline-type binary transformation vectors, co-integrate type transformation vectors, super-binary type transformation vectors, Ri-derived transformation vectors as well as T-DNA carrying vectors used in agrolistic transformation or gene therapy.

The current invention comprises a method for obtaining transgenic eukaryotic cells transformed only with the T-DNA by preventing transfer of vector backbone sequences using said optimized transformation vectors containing any of said modifications (a) to (j).

Further comprised in the current invention is a method for obtaining transgenic eukaryotic cells transformed only with the T-DNA by enabling curing of said transformed cells containing vector backbone sequences using said optimized transformation vectors containing said DNA sequence of (f) or (g) in combination with the supply of a site-specific recombinase or transposase, or of said DNA sequences (h), (i), or (j) eventually in combination with the supply of a site-specific recombinase or a transposase. With curing is meant the removal of transformation vector backbone sequences possibly originating from said vector without abolishing the T-DNA transformation event.

Also part of the invention is a method for obtaining transgenic plants, yeasts, moulds or filamentous fungi which do not contain vector backbone sequences by transforming plants, yeasts, moulds or filamentous fungi with a transformation vector modified according to the invention and/or implying a method of the invention.

The invention further comprises a method for increasing the production by *Agrobacterium* of the nicking complex at least involving VirD1 and VirD2. Said nicking complex components are encoded by the virD-operon (octopine-type or nopaline-type) of which at least one extra copy is integrated in chromosomal and/or extrachromosomal DNA entities contained and maintained within an *Agrobacterium* strain. To decrease T-DNA left border read-through, said method can be applied alone or in conjunction with transformation-vectors containing modified T-DNA borders.

Further comprised in the current invention are any combinations of methods and/or T-DNA vector modifications of the invention to prevent or to cure integration of vector backbone sequences with any other methods and/or T-DNA vector modifications applied to prevent or to cure integration of vector backbone sequences.

Hosts containing said transformation vectors modified according to the present invention, like bacteria, preferably *Agrobacterium tumefaciens* also constitute to the invention.

Also comprising the invention are any combinations of the site-specific recombination system or transposase-mediated recombination system of the current invention to cure integration of vector backbone sequences with the same or any other site-specific recombination system or transposase-mediated recombination system used for any other purpose.

Also comprising within the invention are methods for agrolistic-based transformation of a eukaryotic cell using a T-DNA vector modified according to the alterations as defined in the vectors as mentioned above.

Also comprising within the invention are methods for gene therapy using a T-DNA vector modified according to the alterations as defined in the vectors as mentioned above.

Transgenic plant cells or plants obtainable by an *Agrobacterium*-mediated transformation method as defined above, part of such a plant or progeny thereof also constitute the present invention.

Transgenic yeasts, moulds or filamentous fungi obtainable by an *Agrobacterium*-mediated transformation method as defined above also constitute the present invention.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

*Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

With '*Agrobacterium*' is meant a member of the Agrobacteriaceae, more preferably *Agrobacterium* or Rhizobacterium and most preferably *Agrobacterium tumefaciens*.

With 'T-DNA', or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell. T-DNA strand production is the result of a DNA-processing event initiated by a site-specific nick in a double-stranded molecule. A family of interrelated DNA-processing reactions exists in different prokaryotic systems. In each case, the substrate is a supercoiled circular DNA molecule and the nicking protein recognizes a short sequence, cleaves at a conserved site (conserved nick site positions and consensus region located 3' of the nick), and attaches covalently to the 5' end of the nicked strand. DNA-processing systems that belong to this family include, besides the formation of T-DNA in and transfer of the T-DNA into the eukaryotic cell by *Agrobacterium*, (1) the initiation of conjugative DNA replication and subsequent transfer of plasmids of Gram-negative bacteria, (2) the initiation of plus-strand synthesis during rolling circle replication of φX174-related phage, and (3) the initiation of rolling circle replication in certain plasmids of Gram-positive bacteria (Waters and Guiney 1993). The DNA processing event is catalyzed by an oligoprotein relaxosome complex. One of the proteins in this complex, the relaxase, is the key enzyme catalyzing the site- and strand-specific DNA cleavage (Pansegrau and Lanka 1996). In the case of conjugative transfer of plasmids the relaxase covalently binds to the 5' terminus of the DNA to be transferred and is not able to produce a second nick necessary for transfer of a single copy of the DNA. It is thought that at least a relaxase dimer is required for single copy DNA transfer (Pansegrau and Lanka 1996).

In the case of *Agrobacterium*, a minimum of two proteins are required for nicking and subsequent T-DNA transfer. These relaxosome proteins are VirD1 and VirD2. VirD1 is a type I topoisomerase without sequence specificity (Ghai and Das 1989). The VirD2 protein is, also on the basis of sequence homology, the relaxase of *Agrobacterium* and acts as the nicking endonuclease (Pansegrau et al. 1994). During the nicking process, VirD2 gets covalently attached to both 5' ends of the processed T-DNA at the right border and to the rest of the T-DNA plasmid at the left border (Durrenberger et al. 1989, Young and Nester 1988). Both T-DNA left and right borders are recognized by VirD1 and VirD2. Strong interactions between VirD1 and VirD2 and amongst VirD2 proteins have been demonstrated and it was suggested that T-DNA strand displacement (by DNA replication) is terminated by producing a second nick depending on VirD2-VirD2 interaction. This implies that separate relaxosome complexes including at least VirD1 and VirD2 might be involved in processing each of the two T-DNA borders (Relic et al. 1998).

With 'T-DNA borders', 'T-DNA border region', or 'border region' are meant either right T-DNA border (RB) also referred to as 'right border' or left T-DNA border (LB) also referred to as 'left border'. Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987). Core sequences are as follows (inn: part of T-DNA sequence; out: part of vector backbone sequence; core sequences indicated in bold and underlined capitals; Gielen et al. 1984, 1999):

octopine-type RB: inn-tgatgctgactGGCAGGATATATAC-CGTTGTAATtttgagctcgt-out (SEQ ID NO 1)
  octopine-type LB: out-gcggcagcggaGGCAGGATATAT-TCAATTGTAAAtggcttcatg-inn (SEQ ID NO 2)
  nopaline-type RB: inn-tatcagtgttTGACAGGATATATTG-GCGGGTAAACctaagagaa-out (SEQ ID NO 3)
  nopaline-type LB: out-ggctggctggTGGCAGGATATAT-TGTGGTGTAAACaaattgacg-inn (SEQ ID NO 4)

With 'integral border region' is meant a naturally occurring T-DNA border comprising the border core sequence and both the border inner and outer regions.

With 'T-DNA transformation vector' or 'T-DNA vector' is meant any vector encompassing a T-DNA sequence flanked by a right and left T-DNA border consisting of at least the right and left border core sequences, respectively, and used for transformation of any eukaryotic cell.

With 'vector backbone sequence' or 'vector backbone sequences' is meant all DNA of a T-DNA containing vector that lies outside of the T-DNA borders and, more specifically, outside the nicking sites of the border core imperfect repeats. With 'vector' is meant a transformation vector or T-DNA vector stably maintained in a bacterial culture, e.g. an *Escherichia coli* culture or an *Agrobacterium* culture.

The current invention includes constructs of optimized T-DNA vectors such that vector backbone integration in the genome of a eukaryotic cell is minimized or absent or such that curing of vector backbone sequences integrated in a eukaryotic cell is possible. Said vectors, any derivative thereof or any vector utilizing any of the modifications or any combination of modifications of the present invention can then be used as starting material for cloning of the DNA sequences of interest between the two border repeats and for subsequent applications such as transformation of e.g. a crop plant, a yeast or fungus and such as gene therapy.

With 'optimized T-DNA vector' is meant a T-DNA vector designed either to decrease or abolish transfer of vector backbone sequences to the genome of a eukaryotic cell or to allow curing of vector backbone sequences transferred to the genome of a eukaryotic cell.

In analyses performed in the frame of the current invention (see Examples 1-3), the frequency of vector backbone transfer was compared in transgenic plants that were transformed with T-DNA vectors with border repeats in the natural octopine sequence context, and with T-DNA vectors without the inner border region of the border repeats. Substantially more vector backbone integration was found in the series of transformed plants in which T-DNA vectors without inner border repeat sequences were employed than in the series of transformed plants in which complete inner and outer border regions were used. It was further observed that many transgenic plants contain vector backbone sequences linked to the left T-DNA border as well as vector junctions with the right T-DNA border (see Example 2). DNA gel blot analyses indicate that in most of these plants the complete vector sequence is integrated (see Example 3). Moreover, the frequency of integration of complete vector backbone sequences was not influenced by the presence or absence of the border inner region. These data suggest that the right border inner region most probably does not contain determinants important for efficient nicking at the left T-DNA border. This conclusion is further substantiated by earlier results obtained by Shaw et al. (1984) indicating that deletion of the RB inner region is not influencing efficiency of plant transformation. Determinants for efficient nicking at the left T-DNA border are thus most likely to reside within the LB itself. It is assumed that integration in the plant genome of complete vector backbone sequences is the result of a conjugative transfer initiated at the right border and subsequent continued copying at the left and right borders, called read-through. Vector backbone transfer can also be the consequence of recognition of the LB as a starting point for DNA transfer and continued copying at the RB up to the LB (van der Graaff et al. 1996). It is therefore important to identify LB elements involved in the efficient nicking at the LB core repeat. Thus, e.g. partial or complete deletion of the left border region inner and/or outer regions could put the left border core repeat in a context enhancing its affinity for and recognition by VirD1 and VirD2. A striking observation with respect to this comes from analysis of left (and right) border sequences of the transformation vectors used in experiments described in Examples 2 and 3. In FIG. 1, the percentages of A- and T-residues per 100 bp stretch around (and not including) the LB and RB core repeats is drawn for both transformation vectors with and without the natural border inner region context. The remarkable observation consists of the fact that the percentage of AT-residues of the LB proximal 100 bp of the natural inner region (K T-DNA vector in FIG. 1) is considerably higher than the percentage of AT-residues of the LB proximal 100 bp of the vector in which the natural inner region is deleted (Hsb T-DNA vector in FIG. 1), i.e. 64% compared to 56%, respectively. As mentioned supra, LB read-through and partial vector backbone transfer occurs much more frequently when plants are transformed with Hsb T-DNA vectors when compared to plant transformation with the K T-DNA vector. Mechanistically, it is possible that this lower percentage of AT-residues considerably attenuates the nicking activity of the LB-bound relaxosome including at least VirD1 and VirD2. Concurrently, the DNA replication machinery effecting the T-DNA strand displacement would, at relatively high frequencies, be able to displace the relaxosome from the LB before the nick has been realized. An increased frequency of read-through at the LB would be the consequence of such a process. Thus, the percentage of AT-residues of the 10-100 bp (or preferably 20-100 bp) proximal to the LB and part of the T-DNA is a candidate element of the LB determining the efficiency of nicking at the LB core repeat. For nicking efficiency to be sufficiently high, the percentage of AT-residues of said LB proximal region is to be sufficiently high, i.e. at least about 60-85%, more preferably at least about 64-80%. Although the proximal 100 bp outside of the T-DNA RB core repeat contains a similar percentage of AT-residues as the proximal 100 bp inside of the T-DNA LB core repeat, i.e. 58% compared to 56%, respectively (see FIG. 1), correct and highly efficient processing at the RB is not problematic. This is most likely due to the positive influence of the overdrive sequence present in the RB outer region (Peralta et al. 1986, van Haaren et al. 1987). It is not to be excluded that proteins auxiliary to the relaxosome complex bind to the overdrive sequence and enhance the process of RB nicking. This would again resemble the situation of conjugative plasmid transfer between bacteria where such auxiliary proteins have been identified (Waters and Guiney 1993). It is also not to be excluded that auxiliary proteins, at present not yet identified, are involved in efficient processing of the LB.

The first modified T-DNA vector construct for preventing vector backbone transfer described supra includes an intra-T-DNA LB proximal region enriched in A- and T-residues. Such an approach will, however, not be practicable for all T-DNA constructs. Thus, in FIG. 2, a number of additional optimized T-DNA vector constructs are schematically drawn. Results of plant transformation with the first of the constructs of FIG. 2 are included in the present invention (see Examples 1-3). The other constructs underlie several approaches to obtain optimized T-DNA vectors. The optimizations reside in modifications of the left border design aimed at increasing the efficiency of LB nicking and resulting in vector backbone integration in the genome of a eukaryotic cell that is highly minimized or absent. In said optimized T-DNA vector constructs, the RB region is constant, i.e. it comprises the right border outer region but the right border inner region is deleted. Said right border region contains the 25 bp RB core sequence and the upstream 146 bp of the right border outer region derived from pTiAch5 (Gielen et al. 1984). This outer region contains the overdrive sequence. It is clear that right border regions in their natural context, i.e. comprising the right border inner region can be used as well in the current invention. Right borders from which the border inner regions have been removed have, however, the advantage that transfer to the plant of "foreign" DNA without a clear function and as part of the T-DNA is further limited. Furthermore, it has been discussed supra that the absence of the RB inner region very unlikely influences efficiency of the LB processing. The LB regions in said exemplary optimized T-DNA vectors are generally derived from octopine-type Ti plasmids and all contain a natural left border core sequence. Nopaline-type T-DNA borders are usually derived from Ti-plasmids such as pTiC58 (Gielen et al. 1999). More details about exemplary border regions used in exemplary optimized T-DNA vectors of the invention are described in FIG. 2 and Example 4.

A first embodiment of the invention comprises optimized T-DNA vectors as exemplified in FIG. 2 and including a modification of the T-DNA right border comprising a single right border core sequence flanked by a right border outer region and/or a modification, including multiplication, of the left T-DNA border designed as:

a) a single left border core sequence flanked by a natural left border outer region and an intra-T-DNA left border proximal region with a length of 10 to 100 bp, preferably 20-100 bp, and which is enriched in the number of A- and T-residues, the percentage of AT-residues preferably being 60 to 85%, more preferably being 64 to 80%, most preferably being 65, 66, 67, 68, 69, 70, 71, 72, 73, 74, 75, 76, 78 or 79%, provided that said intra-T-DNA left border proximal region is not the corresponding natural octopine type left border inner region; or, b) a single left border core sequence flanked only by a natural left border inner region; or c) a single left border core sequence; or d) a tandem repeat of several left border core sequences flanked only by a natural left border outer region, with the tandem repeat preferably containing 2-3 left border core sequences but not excluding a higher copy number of the left border core imperfect repeat and with said repeated left border core sequences in said tandem being separate by a sequence of at least 10-20 bp optionally carrying stop codons in the three reading frames and in both directions; or e) an integral nopaline-type left border region adjacent to and downstream or upstream of the integral octopine-type left border region.

Incorporation of modified left border regions displaying efficient nicking at the LB core sequence in commonly used transformation vectors will prevent LB read-through. An additional advantage of the tandem arrangement of the LB core sequences or of integral left borders lies in the fact that occasional read-through or DNA transfer starting at the first copy of said LB core sequence or integral LB region will be terminated at an adjacent copy of said LB core sequence or integral LB region in said tandem. In both cases comprised within the current invention, the frequency of transfer of vector backbone sequences and integration of said sequences in a eukaryotic genome is decreased.

With 'downstream' and 'upstream' are meant any sequences located 5' and 3', respectively, of any other sequence. As a reference, the T-DNA strand is taken which is starting at its 5' end at the RB and terminating at its 3' end at the LB.

Further optimization of T-DNA transformation vectors is envisaged once it is known whether the left border inner and/or outer regions is/are necessary to avoid vector backbone integration. Several deletion derivatives of said inner and/or outer regions can be made to determine which specific sequence(s) in said inner and/or outer border regions is/are important in determining termination of T-DNA transfer. Once this/these sequences is/are known, it/they can be included in more copies around the LB repeat resulting in a more efficient nicking. Such left borders capable of further optimizing T-DNA transformation vectors and said vectors containing said further modified left borders are also subject of the present invention.

The current invention also embodies incorporation of any of said modified left borders in any T-DNA vector comprising binary transformation vectors, super-binary transformation vectors, co-integrate transformation vectors, Ri-derived transformation vectors as well as in T-DNA carrying vectors used in agrolistic transformation or gene therapy.

With 'binary transformation vector' is meant a T-DNA transformation vector comprising:
a) a T-DNA region comprising at least one gene of interest and/or at least one selectable marker active in the eukaryotic cell to be transformed; and
b) a vector backbone region comprising at least origins of replication active in *E. coli* and *Agrobacterium* and markers for selection in *E. coli* and *Agrobacterium*.

Alternatively, replication of the binary transformation vector in *Agrobacterium* is dependent on the presence of a separate helper plasmid. The binary vector pGreen and the helper plasmid pSoup form an example of such a system as described in e.g. Hellens et al. (2000), Plant Mol. Biol. 42, 819-832, or as available on the internet site www.pgreen.ac.uk.

The T-DNA borders of a binary transformation vector can be derived from octopine-type or nopaline-type Ti plasmids or from both. The T-DNA of a binary vector is only transferred to a eukaryotic cell in conjunction with a helper plasmid.

With 'helper plasmid' is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With 'super-binary transformation vector' is meant a binary transformation vector additionally carrying in the vector backbone region a vir region of the Ti plasmid pTiBo542 of the super-virulent A. tumefaciens strain A281 (EP0604662, EP0687730). Super-binary transformation vectors are used in conjunction with a helper plasmid. With 'co-integrate transformation vector' is meant a T-DNA vector at least comprising:
a) a T-DNA region comprising at least one gene of interest and/or at least one selectable marker active in plants; and
b) a vector backbone region comprising at least origins of replication active in *Escherichia coli* and *Agrobacterium*, and markers for selection in *E. coli* and *Agrobacterium*.

The T-DNA borders and said set of vir genes of a said T-DNA vector can be derived from either octopine-type or nopaline-type Ti plasmids or from both.

With 'Ri-derived plant transformation vector' is meant a binary transformation vector in which the T-DNA borders are derived from a Ti plasmid and said binary transformation vector being used in conjunction with a 'helper' Ri-plasmid carrying the necessary set of vir genes.

With 'agrolistics', 'agrolistic transformation' or 'agrolistic transfer' is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; WO97/12046).

Two possible mechanisms leading to transfer and integration of vector backbone sequences in an eukaryotic genome are recognized. In a first mechanism, T-DNA transfer legitimately starts at the right T-DNA border but does not stop at the left T-DNA border and is followed by continued copying of vector backbone sequences. This mechanism is known as left border read-through. In a second mechanism, DNA transfer is illegitimately initiated at the left T-DNA border with continued copying till the left T-DNA border is reached again. Irrespective of which mechanism prevails, analysis of transgenic plants indicates that many of them have the complete vector backbone sequences integrated into their genome. The present invention further describes an approach to cure transformed cells containing vector backbone sequences by recombination involving a recombinase and recombination sites.

With 'curing' is meant here the removal of transformation vector backbone sequences without abolishing the T-DNA integration event. Another tool for the elimination of non-T-DNA sequences from transgenic individuals has been described by Hanson et al. (1999). This tool is, however, different and not related to the curing method described in the present invention. As discussed supra, elimination of non-T-DNA sequences according to the methods of Hanson et al. (1999) or WO99/01563 has the drawback of decreasing the transformation efficiency (Hanson et al. 1999).

Thus, in another embodiment of the invention, curing of transformed cells is obtained by a recombination event as the method for removing the illegitimately integrated vector backbone sequences. As a result, transformed cells are obtained which retain the T-DNA in their genome. Contrary to the methods of Hanson et al. (1999) or WO99/01563, the curing method of the current invention rescues T-DNA containing transgenic cells which previously carried illegitimately integrated vector backbone sequences. Transformation efficiencies are thus hardly affected.

With 'recombination event' is meant either a site-specific recombination event or a recombination event effected by transposon 'jumping'.

With 'recombinase' is meant either a site-specific recombinase or a transposase.

With 'recombination site' is meant either site-specific recombination sites or transposon border sequences.

With 'site specific recombination event' is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of vector backbone sequences integrated into a eukaryotic genome, such integration of said sequences can subsequently be removed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from Shigella, and the R/RS system of *Zygosaccharomyces rouxii*. Recombinases generally are integrases, resolvases or flippases. Also dual-specific recombinases can be used in conjunction with direct or indirect repeats of two different site-specific recombination sites corresponding to the dual-specific recombinase (WO99/25840).

The preferred site-specific recombinase systems are the bacteriophage P1 Cre/lox and the yeast FLP/FRT and the *Z. rouxii* R/RS systems. In these systems a recombinase (Cre, FLP or R, respectively) interact specifically with its respective site-specific recombination sequence (lox, FRT or RS respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990, Onouchi et al. 1991, Sugita et al. 2000) and *Arabidopsis* (Osborne et al. 1995, Onouchi et al. 1995). Site-specific recombination systems have many applications in plant molecular biology including methods for control of homologous recombination (e.g. U.S. Pat. No. 5,527,695), for targeted insertion, gene stacking, etc. (WO99/25821) and for resolution of complex T-DNA integration patterns or for excision of a selectable marker (WO99/23202). In these applications the site-specific recombination sites are typically part of the DNA integrated in the eukaryotic genome as T-DNA or via homologous recombination, and thus are not present in the vector backbone sequence.

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

As part of the current invention, site-specific recombination sites are introduced in the T-DNA vector such that they lie outside the T-DNA but allow transferred vector backbone sequences or parts thereof possibly originating from said T-DNA vector to be excised post-transformationally by the action of a site-specific recombinase.

With 'recombination event effected by transposon jumping' or 'transposase-mediated recombination' is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987). Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are introduced in the T-DNA vector such that they lie outside the T-DNA and transform the vector backbone or part thereof into a transposon-like entity that can move by the action of a transposase.

As transposons, and thus in the current invention the vector backbone or part thereof, often reintegrate at another locus of the host's genome, segregation of the progeny of the hosts in which the transposase was allowed to act might be necessary to separate transformed hosts containing only the T-DNA and transformed hosts containing only the vector backbone or part thereof.

Another embodiment of the invention comprises optimized T-DNA transformation vectors with additional DNA sequences outside the T-DNA border core repeats as exemplified in FIG. 3 and enabling post-transformational removal of integrated vector backbone sequences. Said additional DNA sequences modify, including multiply, the T-DNA border regions or parts thereof and comprise:

f) recombination sites organized as repeats downstream of the left border core sequence and upstream of the right border core sequence; or g) said DNA sequences of (f) further modified by adding a second copy of a left border region positioned upstream of and preferably adjacent to the single right border outer region and said recombination site upstream of the core sequence of said second left border region; or h) said recombination sites of (f) with a recombinase gene, downstream of said recombination site downstream of the left border core sequence, and preferably, when present, adjacent to and downstream of the left border outer region; or i) a DNA sequence located downstream of the left border region, said DNA sequence comprising a recombinase gene flanked by repeats of recombination sites as defined in (h) and further comprising a second copy of a left border region downstream of said recombinase; or j) the DNA sequence of (i) with additional recombination sites organized as repeats downstream of the second left border core sequence and upstream of the single right border core sequence;

In any of said modifications (f), (g), (h), (i) or (j), said recombination sites are located adjacent to and downstream and/or upstream of the left- and/or right border core sequences or are separated from the left- and/or right border core sequences by a sequence of at least 10-20 bp in length optionally carrying stop codons in the three reading frames and in both directions.

In any of said modifications (f), (g), (h), (i) or (j), said recombination sites are either site-specific recombination sites arranged as direct repeats or transposon border sequences arranged as inverted repeats and said recombinase gene is either a site-specific recombinase gene or a transposase gene, respectively.

It is obvious that said modifications (f) or (g) in said T-DNA transformation vectors are to be considered as simple modifications, including multiplication, of the T-DNA border regions or parts thereof.

Introduction of additional DNA sequences downstream of the T-DNA left border core repeat to prevent left border read-through (WO99/01563) or to eliminate non-T-DNA sequences (Hanson et al. 1999) have been described and these sequences prevent the development of transformants having integrated vector backbone sequences. In addition to said modifications (f), said modification (g) of the T-DNA vector has the advantage that read-through at the first LB core sequence can be halted at the second LB core sequence, thus preventing duplication of the T-DNA fragment. Inserted vector backbone sequences are subsequently removed by the action of an appropriate recombinase. In addition to said modifications (f), said modification (h) introduces in a T-DNA vector a recombinase gene sequence downstream of the left border core sequence to allow for resolving the integrated vector backbone sequence possibly originating from said T-DNA vector at the recombination sites introduced in said modified T-DNA borders. Thus, and contrary to WO99/01563, transformants having integrated vector backbone sequences can be rescued after curing, i.e. after removal of the vector backbone sequences flanked by the recombination sites introduced in said modified T-DNA borders. Concurrently, the recombinase gene is excised.

Said modifications (i) further change the design of the left border region, i.e. an additional copy of a left border region is added. Both copies are, however, not arranged in tandem as described supra in the first approach to prevent vector backbone integration, but are separated by the recombinase gene and the border core sequences are occurring in their broader border context. Said modifications (i) are thus to be considered as a modification of the T-DNA vector construct described supra in which the single LB region contains a tandem arrangement of the LB core sequence.

The presence of a second copy of a left T-DNA border region has the advantage that illegitimate DNA transfer starting at or read-through at the first left border core sequence can be halted at the second left border core sequence. Thus, only part of the vector backbone sequence is transferred to the eukaryotic nucleus. As this vector backbone region is flanked by recombination sites, it can easily be removed by means of action of a recombinase. Illegitimate DNA transfer starting at or read-through at the second copy of the left border core sequence can, however, still occur.

Therefore, said modification (j) further adds a pair of recombination sites downstream of the second copy of the left border core sequence and upstream of the single right border region. Integrated vector backbone sequences can again be easily removed by action of a recombinase at the recombination sites. In the case of illegitimate DNA transfer starting at the second copy of the left border core sequence, the recombinase will not be supplied by the T-DNA transformation vector backbone. It must thus be supplied from elsewhere, e.g. through sexual crossing with a plant already containing the recombinase gene in it's genome.

Any of said modifications (f), (g), (h), (i) or (j) is also applicable to cure transgenic cells from vector backbone sequences integrated into the genome of a eukaryote independently of the T-DNA, i.e. not physically linked to the T-DNA.

Further comprised in the- current invention is a method using said T-DNA transformation vectors containing said DNA sequences of (f) or (g) in combination with the supply of a recombinase, or using said T-DNA transformation vectors containing said DNA sequences (h), (i) or (j) for curing of transformed cells containing backbone sequences of said vector backbone sequences optionally in combination with the supply of a recombinase.

Site-specific recombinases or transposases introduced into the host's genome for enabling recombination can subsequently be removed by segregation of the progeny of the transformed host in which recombination was allowed to occur. Segregation of said progeny also is a way to separate transformed hosts containing only the T-DNA and transformed hosts containing only the vector backbone or part thereof.

The current invention further embodies incorporation of any of said additional DNA sequences in any T-DNA vector comprising binary transformation vectors, super-binary transformation vectors, co-integrate transformation vectors, Ri-derived transformation vectors as well as in T-DNA carrying vectors used in agrolistic transformation or gene therapy.

In one embodiment of the current invention, the recombinase gene is supplied to the transgenic plants containing a vector backbone sequence flanked by recombination sites by sexual crossing with a plant containing the recombinase gene in it's genome. Said recombinase can be operably linked to either a constitutive or an inducible promoter. The recombinase gene can alternatively be under the control of single subunit bacteriophage RNA polymerase specific promoters, such as a T7 or a T3 specific promoter, provided that the host cells also comprise the corresponding RNA polymerase in an active form. Yet another alternative method for expression of the recombinase consists of operably linking the recombinase open reading frame with an upstream activating sequence fired by a transactivating transcription factor such as GAL4 or derivatives (U.S. Pat. No. 5,801,027, WO97/30164, WO98/59062) or the Lac repressor (EP0823480), provided that the host cell is supplied in an appropriate way with the transcription factor.

In another embodiment of the invention, the recombinase gene is supplied on the transformation vector backbone and the promoter of said recombinase gene preferably is an inducible promoter. Such promoters are known to those familiar with the art and include e.g. a heat-shock responsive promoter, a glucocorticoid-inducible promoter or a promoter inducible by another chemical compound (e.g. as disclosed in EP0332104 and WO90/08826).

In a preferred embodiment, expression of the recombinase gene in bacterial hosts is prohibited by including (an) intron sequence(s) in the coding region of said recombinase gene.

It is known in the art that increased levels of VirD1 and VirD2 in *Agrobacterium* lead to higher levels of plant transformation (Wang et al. 1990). VirD1 and VirD2 have also been integrated in a method for improved integration of exogenous DNA delivered to eukaryotic cells by means of transforming said eukaryotic cell with chimeric virD1 and/or virD2 genes (WO97/12046). It has, however, so far not been demonstrated that increased production of VirD1 and/or VirD2 can prevent integration of vector backbone sequences.

Thus, in another embodiment of the invention, vector backbone sequence integration is prevented by enhancing the efficiency of the nicking at the left border core sequence of a T-DNA vector by increasing the production of the T-DNA nicking complex involving at least endonucleases VirD1 and VirD2.

In a preferred embodiment of the invention, additional copies of the octopine-type virD locus are integrated either into the genome of *Agrobacterium* and/or into a helper plasmid and/or into a binary transformation vector and/or into a superbinary transformation vector and/or into a co-integrate transformation vector and/or a Ri-derived plant transformation vector. In another embodiment of the invention, additional copies of the nopaline-type virD locus can be supplied as said.

The current invention thus presents three methods either to prevent or to cure integration of transformation vector backbone sequences and using:

1) any of the T-DNA vectors (a) to (e) modified at the left T-DNA border region such that read-through is prevented or halted or DNA-transfer starting at this border is prevented or halted; or
2) any of the T-DNA vectors (f) to (j) which enable resolving of transformation vector backbone sequences integrated in the genome of transgenic cells by means of recombination; or
3) at least one extra copy of the virD locus in *Agrobacterium* to increase the levels of VirD1 and VirD2 as minimal constituents of the T-DNA border nicking complex.

It is clear to those familiar with the art that any of these methods or parts thereof can be used either alone, in combinations of two, or as a combination of all three of them. Exemplary T-DNA vector designs reflecting some of such combinations are given in FIG. 3.

Preferred combinations of the inventive methods (1) or (2) with inventive method (3) consist of a transformation vector carrying a modified LB region containing a tandem arrangement of the LB core sequence or multiple copies of the LB region and the enhanced production of VirD1 and VirD2 by *Agrobacterium*. It can indeed be expected that the tandem of LB core sequences or the multiple copies of the LB region titrate the VirD1 and VirD2 proteins available in an *Agrobacterium* strain normally used for transformation. As a result, these proteins would no longer be available for establishing the nick at the single RB core sequence.

Another embodiment of the invention thus comprises the use of any of said methods and/or T-DNA vector modifications to prevent or to cure transformation vector backbone integration either separately or in any combination. Preferred combinations are those in which enhanced levels of VirD proteins produced by *Agrobacterium* are allowed to act on T-DNA vectors harboring multiple copies of the LB core sequence or multiple copies of the LB regions.

It is also clear that any of said methods and/or T-DNA vector modifications to prevent or to cure vector backbone integration can be combined with any other method preventing or curing vector backbone integration. Such methods and T-DNA vector modifications include the addition of genes or DNA sequences downstream of the left border, e.g. as disclosed in WO99/01563. Such genes/DNA sequences include genes encoding cytotoxic compounds, antisense housekeeping genes, sequences prohibiting unwinding of the DNA behind the left border region, e.g. sequences with high GC content or vir box sequences interacting with DNA-binding proteins.

Another embodiment of the invention thus comprises the use of any of the methods and/or T-DNA vector modifications of the current invention to prevent or to cure integration of transformation vector backbone sequences in combination with any other method and/or T-DNA transformation vector modification to prevent or to cure transformation vector backbone integration.

It will furthermore be clear to the one skilled in the art that any of the methods and/or T-DNA vector modifications of the current invention to cure integration of transformation vector backbone sequences can be combined with any other method and/or T-DNA vector modification using or incorporating any recombination systems, e.g. to excise selectable markers active in plants. Said curing method can indeed be combined with e.g. excision of a selectable marker by flanking the exemplary selectable marker either with the same or with different recombination sites as those flanking the vector backbone sequence. In said curing method, the vector backbone sequence can also be flanked by two different site-specific recombination sites and curing can be performed by a dual-specific recombinase with specificities corresponding to the site-specific recombination sites used.

A further embodiment of the current invention thus comprises the use of the methods and/or T-DNA vector modifications of the current invention to cure integration of transformation vector backbone sequences in combination with methods and/or T-DNA vector modifications using or incorporating any recombination system for purposes other than curing of vector backbone sequence integration.

Another embodiment of the current invention comprises curing of integrated transformation vector backbone sequences implying modification of the T-DNA borders by adding any pair of mutually different site-specific recombination sites and used in conjunction with an at least dual-specific recombinase with specificities at least corresponding to the site-specific recombination sites used.

In another embodiment of the invention, any of said T-DNA vector constructs according to the invention is mobilized to an *Agrobacterium* strain. The resulting strains also constitute to the invention.

In yet another embodiment of the invention, any of said T-DNA vectors according to the invention is used in an *Agrobacterium*-mediated or agrolistic transformation, such transformation methods being known to the one skilled in the art. Said T-DNA vectors according to the invention can be used to transform several plant tissues comprising roots, protoplasts, leaves etc. of different monocotyledonous and dicotyledonous plant species such as, but not limited to, *Arabidopsis*, tobacco, petunia, tomato, potato, beans, rice and wheat. More in general, it can be any monocotyledonous or dicotyledonous plant, preferbly belonging to a plant species of interest in agriculture, wood culture, horticulture or to a plant species applied in the production of pharmaceuticals, biochemicals, antibodies or perfumes. Such plants include crop plants, root plants, oil-producing plants, wood-producing plants, agricultured plants, fruit-producing plants, fodder or forage legumes, companian plants or horticultured plants. Such plants further include apricot, artichoke, asparagus, apple, banana, barley, broccoli, Brussels sprouts, cabbage, canola, carrot, cassava, cauliflower, celery, cherry, chicory, collard greens, cotton, Douglas fir, fir (Abies and Picea species), flax, garlic, grapes, kale, lentil, maize, oak, oats, oilseed rape, okra, onion, pear, pepper, poplar, rye, sorghum, soybean, squash, sugar beet, sugar cane, sunflower.

Said T-DNA vectors according to the invention can also be used in combination with the flower dip plant transformation method (Clough and Bent 1998) or with the in planta apical shoot transformation procedure (WO99/14348). Said T-DNA vectors according to the invention can also be used to transform other eukaryotic cells including yeast, moulds and filamentous fungi and their conidia, hyphae or protoplasts derived thereof.

*Agrobacterium*-mediated transformation of said other eukaryotic cells is known to those skilled in the art (e.g. WO98/45455). A key characteristic of the eukaryotic cells transformed via *Agrobacterium*-mediated transfer or agrolistic transfer of any of the T-DNA transformation vectors of the invention is a significantly decreased frequency of integrated vector backbone sequences without greatly affecting the frequency of integration of T-DNA sequences.

A preferred embodiment of the invention comprises transgenic plant cells obtained by any method of *Agrobacterium*-mediated transfer or agrolistic transfer of any of the T-DNA transformation vectors of the invention. Also comprised are the transgenic plants obtained or regenerated by any method after any method of *Agrobacterium*-mediated transfer or agrolistic transfer of any of the T-DNA transformation vectors of the invention. Such plants are characterized in that they contain T-DNA sequences, but not vector backbone sequences, in their genome. Further comprised are the offspring of said transgenic plants as well as cells, protoplasts, calli, tissues, organs, seed, fruit, pollen, egg cells, zygotes, zygotic or somatic embyros derived thereof or derived from said transgenic plant cells.

The potential for using T-DNA carrying vectors according to the present invention in gene therapy can be explained as follows. It has been described that in vitro reconstituted complexes consisting of VirD2-ssDNA-VirE2 are able to transfer the ssDNA intactly into mammalian nuclei (Ziemienowicz et al. 1999).

Vir D2 protects ssDNA against exonucleolytic degradation because it is covalently linked to the 5' end of the ssDNA (Durrenberger et al. 1989, Young and Nester 1988) and, by means of two nuclear localization sequences (NLSs), targets the ssDNA to the plant cell nucleus (Narasimhulu et al. 1996, Rossi et al. 1993, Shurvinton et al. 1992).

VirD2 furthermore contains an 'omega' domain important for efficient integration of the T-DNA in the host genome (Narasimhulu et al. 1996, Mysore et al. 1998, Tinland et al. 1995). The NLSs of VirD2 have been shown to be active in animal cells including human HeLa cells, Drosophila embryos and Xenopus oocytes (Guralnick et al. 1996, Ziemienowicz et al. 1999). VirD1 remains localized in the cytoplasm of mammalian cells but can be imported into the nucleus via a piggy-back mechanism involving VirD2 (Ziemienowicz et al. 1999).

VirE2 protects ssDNA against (endo)nucleolytic degradation and preserves integrity of the T-DNA (Gelvin 1998b, Rossi et al. 1996). The VirE2 protein is furthermore actively involved in targeting the T-DNA to the plant nucleus (Gelvin 1998b). The NLSs of VirE2 may be plant specific but repositioning of a single amino acid within the VirE2 NLSs targets these modified proteins to the nuclei of animal cells (Guralnick et al. 1996).

VirE2 proteins interact amongst themselves but interaction of VirE1 with VirE2 is much stronger and VirE1 inhibits VirE2 self-interaction. In *Agrobacterium* cells, VirE1 prevents VirE2 from aggregating. VirE1 thus seems to function as a molecular chaperone of VirE2 (Deng et al. 1999).

The characteristics of these Vir proteins make them ideal candidates for their application in gene therapy experiments as indicated by Ziemienowicz et al. (1999).

One of the main problems in gene therapy indeed consists of the difficulty of DNA-delivery across the intracellular barriers including nucleolytic degradation and nuclear uptake.

Viral vectors are one of the major vehicles used by scientists in gene therapy to get a DNA sequence expressed in the proper host. Retroviral vectors (including HIV and MMLV) are employed in 63% of the gene therapy protocols approved by the Recombinant DNA Advisory Committee (a division of the NIH) whereas adenoviral vectors are used in 16% of such protocols. Other viral vectors include those based on AAV, HSV and Vaccinia. Viral vectors form an area of continual new development in gene therapy.

It can be envisaged that the genes for the *Agrobacterium* proteins VirD1, VirD2 and VirE2 (and eventually VirE1) are incorporated in a viral vector in such a way (i.e. including adapted codon usage and appropriate regulatory sequences) that they can be expressed in animal cells, preferably transiently, as preferably without integration of said vir-genes in the host's genome. If a T-DNA containing the gene of interest for gene therapy purposes, is present in the same viral vector or is co-delivered on a separate viral vector or another type of viral vector, said T-DNA could be then efficiently transferred to the genome in nuclei of animal cells. A strict requirement for approval of such a gene therapy strategy would, however, be that only the T-DNA, and not any other external DNA is transferred to the nucleus. Any modification presented in the current invention to prevent or to cure transfer of DNA sequences not belonging to the T-DNA would thus be of great value for increasing the acceptability of gene therapy strategies that include the use of *Agrobacterium* proteins for providing and transferring the DNA of interest. Therefore, T-DNA carrying vectors modified according to any of the modifications or any combination of modifications of the current invention and being used for gene therapy purposes are included in the present invention.

It is furthermore clear to the skilled artisans that at least the T-DNA vectors according to the current invention and comprising modified LBs resulting in highly efficient nicking at this LB can be utilized as a source of e.g. VirD2—ss-T-DNA—VirE2 complexes that can be used in other gene therapy techniques including microinjection, electroporation, carrier mediated delivery and ballistic DNA injection. Said complexes could be enriched from e.g. an acetosyringone-induced *Agrobacterium* culture or a culture of *E. coli* expressing at least the VirD1, VirD2 and VirE2 proteins by means of e.g. affinity chromatography using an antibody recognizing the VirD2 protein.

The invention, now being generally described, may be more clearly understood by reference to the following examples, which are included merely for purposes of illustration of certain aspects and embodiments of the present invention and are not intended to limit the invention. The contents of all references referred to in this text are hereby incorporated by reference.

(A) Schematic representation of the digest and the probe used in the DNA gel blot analysis (not drawn to scale). Each plant genomic DNA sample and the plasmids used as positive controls were digested with KpnI and SacI, both cutting in the vector backbone outside the LB and RB. As probe the vector sequence of the K plasmid, shown as a hatched bar, was used after restriction with KpnI and SacI.

(B) DNA gel blot analysis. The T-DNA vectors of which at least 1000 bp vector backbone was found via PCR analysis of the transgenic plants are indicated at the top of each lane. A fragment of 8476 bp (arrow 1) is observed when the entire vector backbone sequence of the K plasmid (K1 and K2 carry a different structural gene in their T-DNA but are furthermore identical) is integrated, whereas fragments of 7066 bp (arrow 2) are detected when the entire vector backbone sequence of the Hsb plasmid is integrated. The K and Hsb T-DNA plasmids are described in Example 1.

Figure 6:
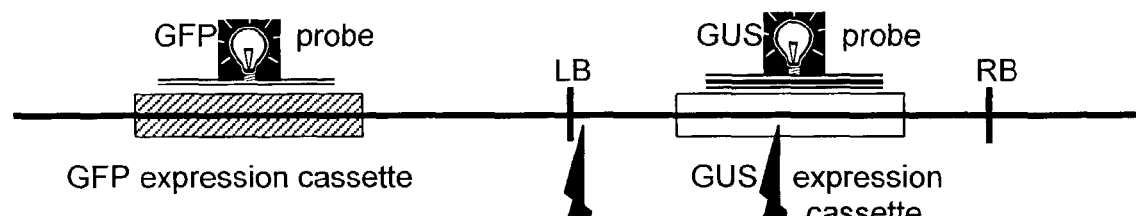
Figure 6:
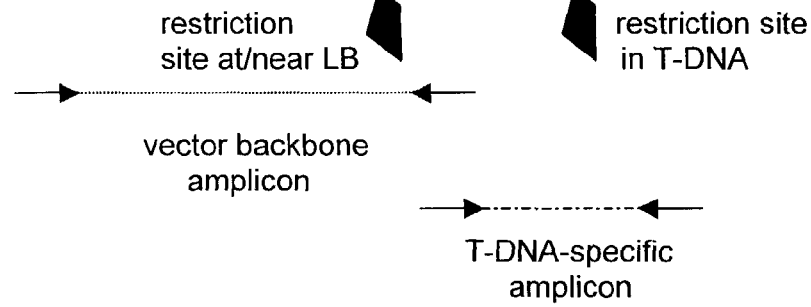

FIG. 6. Schematic overview of the experimental setups for the hybridization and PCR approaches of analysis of the production of ssT-DNA strands as described in Example 6.

Genomic DNA samples in lanes 1, 2 and 5 are derived from plants from experiments other than those described.

Lane C: genomic DNA of untransformed *A. thaliana*.

Plasmid lanes: contain pure DNA of the indicated plasmids digested with KpnI and SacI.

EXAMPLES

Example 1

Transformation of *A thaliana* (L.) Heynh and *Nicotiana tabacum* (L.)

Plasmids pK2L610 ('K' T-DNA vector; De Buck et al. 1998), pSingle gus ('Ksb1' T-DNA vector; see below) and pHSB610 ('Hsb' T-DNA vector; De Buck et al. 1999) were used for plant transformation. The vector pSingle gus ('Ksb1') is similar to the vector pHSB610 ('Hsb') but the Pnos-hpt-3'nos fragment of pHSB610 ('Hsb') is exchanged for a Pnos-nptII-3'nos cassette in pSingle gus ('Ksb1'). As a selectable marker for plant transformation, the K and Ksb1 vectors contain the neomycin phosphotransferase II gene (nptII) and the Hsb vector contains the hygromycin phosphotransferase gene (hpt). *A. thaliana* was co-transformed with plasmids K and Hsb according to the *Agrobacterium*-mediated *Arabidopsis* root transformation method (De Buck et al. 1999, Valvekens et al. 1988). Tobacco (*N. tabacum*) was transformed with plasmid Ksb according to the *Agrobacterium*-mediated leaf disc transformation method (Horsch et al. 1985). Transgenic plants were regenerated on media containing the appropriate plant growth hormones and the appropriate selective agent. In series 1, 18 transgenic *A. thaliana* plants co-transformed with the K and Hsb T-DNA vectors were obtained. In series 2, 36 *N. tabacum* plants transformed with the Ksb T-DNA vector were obtained. In an additional series, 26 *N. tabacum* plants transformed with the Ksb T-DNA vector were obtained.

Example 2

Integration of Vector Backbone Sequences Assessed by PCR

For PCR analysis, DNA was isolated from leaf material of *N. tabacum* as described by Jones et al. (1985) and from *A. thaliana* according to De Neve et al. (1997). To screen the transgenic plants on the integration of vector sequences, different PCR reactions were performed. DNA (100 ng) was incubated with 500 ng of each primer in 1× Taq polymerase incubation buffer (Roche Diagnostics, Brussels, Belgium). Two and a half units of Taq polymerase were added to a final volume of 100 μL. Samples were heated to 94° C. for 5 min before PCR. Denaturation was at 94° C. for 1 min. Annealing occurred during 2 min at 57° C., and the extension reaction was at 72° C. for 5 min, while 30 cycli were performed. The primer combinations were chosen so that the presence of at least 100 bp ('RB100' and 'LB100' in Tables 1 and 2) or at least 1000 bp ('LB1000' and 'RB1000' in Tables 1 and 2) of vector backbone results in a diagnostic PCR fragment of known size. To make sure that the amplified PCR product is not derived from contaminating *Agrobacterium* cells that would still be present in the plant tissue, a PCR reaction was performed on each DNA with two primers specific for the chromosomal *A. tumefaciens* gene picA (Yusibov et al. 1994).

The series 1 *A. thaliana* plants contains 18 transgenic plants co-transformed with the K and the Hsb T-DNA vectors. The K vector contains borders in the natural octopine context with inner and outer border regions of 150 bp and 255 (RB)-300 (LB) bp, respectively, whereas the Hsb vector contains only the outer border regions. Screening for the integration of vector backbone sequences was revealed that vector sequences from the K and Hsb T-DNAs were found in 33% (6/18) and in 61% (11/18) of the transgenic plants, respectively. Only in one transformant the vector sequences were not linked to the T-DNA. No major differences were detected in frequencies of vector joined to the RB region of the Hsb (6/18) and the RB (4/18) region of the K plasmid (see Table 1). However, much more vector was integrated at the LB region of the Hsb T-DNA (11/18) than of the K T-DNA. In all cases, in which an integrated T-DNA contains vector sequences at the RB, also vector sequences at the LB could be detected.

The series 2 tobacco plants contains 36 transgenic plants transformed with a Ksb vector. This vector contains also RB and LB without inner border regions and is therefore comparable to the Hsb vector. In 53% (19/36) of the analyzed transformants (see Table 2) vector sequences were found; these were linked to the LB (8/19) only, to the right T-DNA end (1/19) only, or to both ends (10/19).

In another series of tobacco transformants containing the Ksb T-DNA (data not shown), 81% of the transformants (21/26) contained vector sequences linked at the LB and 61% (16/26) linked at the RB (data not shown). Strikingly however, of these 16 transformants containing RB backbone sequences, 15 of them contain also integrated LB vector sequences (data not shown).

Taken together, in the three different series of transformants in which a T-DNA vector was used without, inner border sequences, more than 50% of the transformants contained vector backbone DNA. Very few transformants contained vector DNA linked only to the right T-DNA end. In general, when vector DNA linked to the right border was present, also vector DNA linked at the left T-DNA end could be detected. This implies that especially read-through at the left border repeat, due to inefficient nicking is responsible for the integration of vector backbone sequences. It is possible that the deletion of the inner border region, a piece of T-DNA present in the original Ti plasmid form which the vector was derived, causes inefficient nicking of the LB repeat, which results in read-through past the LB and the transfer of downstream-located vector sequences. Consistently, Horsch and Klee (1986) observed that the overal rate of transfer to plants of plasmids containing only the 25 bp repeat is not as high as with the larger Ti-derived border fragments, suggesting that additional sequences surrounding the border repeats play some role in the transfer. These authors have, however, not addressed the question of possible integration of vector backbone sequences in transgenic plants using said vector.

Example 3

Integration of Vector Backbone Sequences Assessed by DNA Gel Blotting

Figure 5:
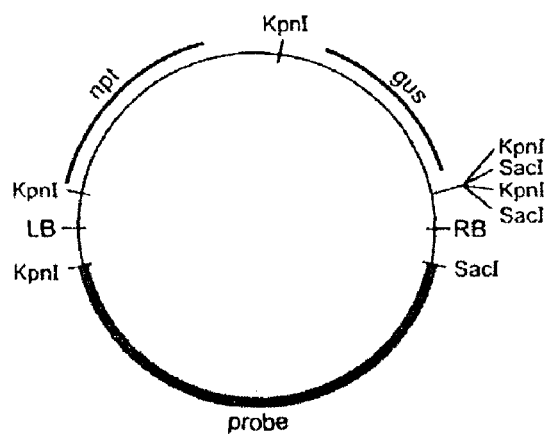
FIG. 5. DNA gel blot analysis.
Figure 5:

DNA gel blot analysis was performed essentially according to Maniatis et al. (1982) on approximately 0.6 µg genomic DNA. The restriction sites used (KpnI-SacI) are indicated in FIG. 5A. As probe, the vector sequence of the K plasmid was used after restriction with KpnI and SacI. The non-radioactive "Gene images" random prime labelling module and the "Gene images" CDP Star detection module (Amersham, Aylesburg, UK) were used for the hybridization and the detection, respectively. As outlined in Example 2, linkage of both RB and LB regions to at least a 1000 bp vector backbone fragment of one or both plasmids was observed in different transformants of series 1 (see Table 1). To determine whether the complete binary T-DNA plasmid (T-DNA+vector backbone sequences) is integrated into the genome of these transformants, a DNA gel blot analysis was performed with the K vector sequence as probe. When the whole vector sequence is present, restriction of the genomic DNA with KpnI and SacI should result in the detection of a fragment of approximately 8467 bp for K (arrow 1 in FIG. 5B) and of 7066 bp for Hsb (arrow 2 in FIG. 5B). The DNA gel blot analysis given in FIG. 3B shows that in 10 of the 11 analyzed plants, the whole vector backbone sequence backbone was integrated into the plant genome. Samples in lanes 1, 2 and 5 are derived from plants from experiments other than those described. These results suggest that complete vector sequences are frequently integrated into the plant genome.

Example 4

Construction of Optimized T-DNA Vectors with Modified Left Borders.

Exemplary optimized binary T-DNA vectors with modifications of the types indicated in FIG. 2 were constructed as follows.

In this example, all optimized binary T-DNA vectors described in this example are derived from pTHW136. The binary vector pTHW136 contains octopine-type right and left border core sequences forming an imperfect repeat, each flanked by octopine-type border outer regions originating from pTi15955 (224 bp in the case of the RB outer region and 268 bp in the case of the LB outer region). On the T-DNA of pTHW136 are located a GUS-intron expression cassette (35S promoter-GUS open reading frame interrupted by an intron-35S terminator) and a nptII selectable marker gene (nos promoter-nptII open reading frame-ocs terminator).

Figure 1:
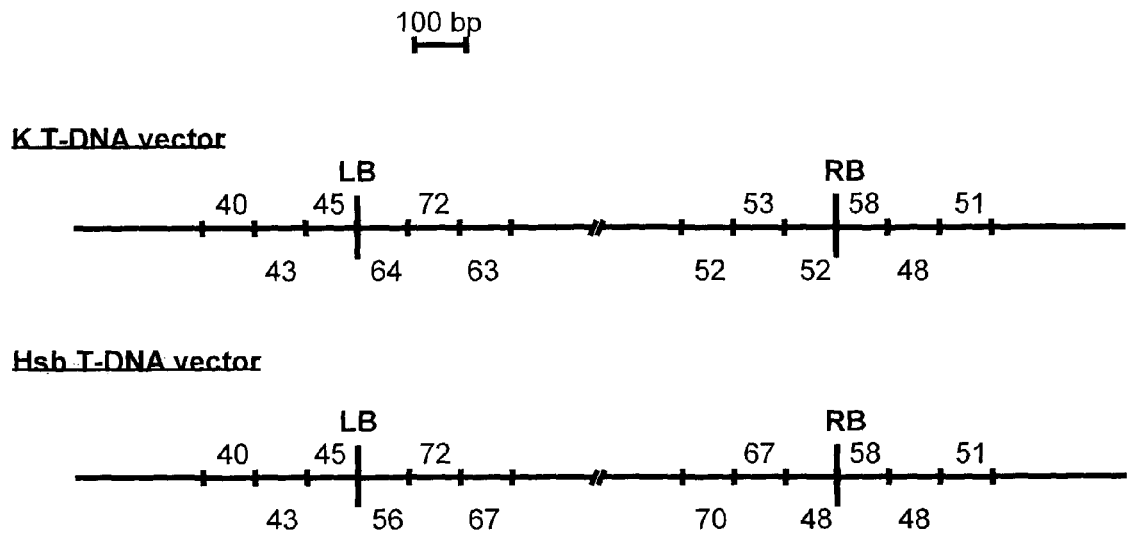
FIG. 1. Schematic representation of the percentage of A- and T-residues (indicated above and below the horizontal line indicating the vector) per 100 bp blocks around (and not including) left and right border core imperfect repeats of the K and Hsb T-DNA vectors described and used in Examples 1-3.
Figure 2:
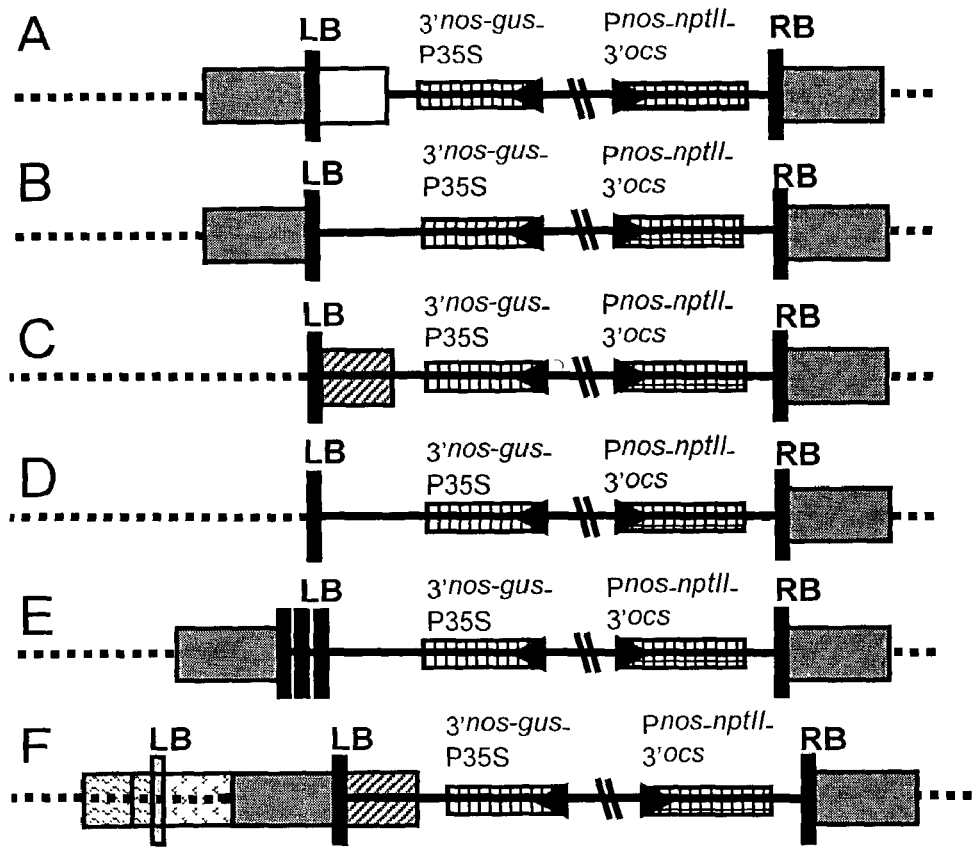
FIG. 2. Schematic representation of T-DNA constructs designed to asses the efficiency of nicking at the modified left border in conjunction with a right border lacking the border inner region. Gus: β-glucuronidase coding sequence; nptII: neomycin phosphotransferase II coding sequence; 3' ocs: 3' terminator of the octopine synthase gene; Pnos: promoter of the nopaline synthase gene; 3' nos: 3' terminator of the nopaline synthase gene; P35S: constitutive 35S RNA promoter of the cauliflower mosaic virus.
Figure 2:
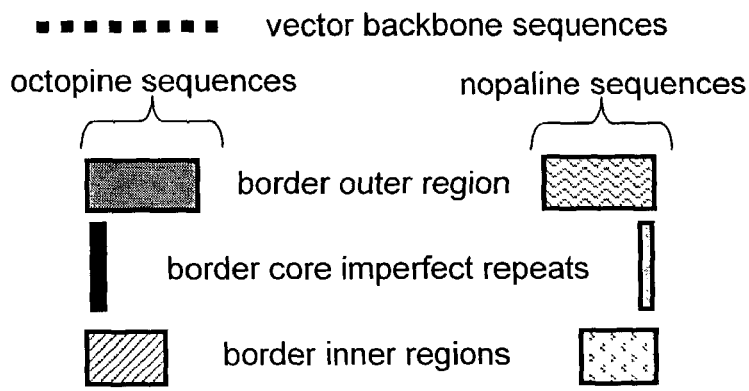
Figure 2:

To create exemplary binary T-DNA vectors of the types indicated in FIG. 2, the GUS-intron expression cassette was removed from pTHW136 by digestion with XbaI and HindIII, followed by filling in the overhangs with the Klenow polymerase and by religation of the resulting blunt ends. The vector obtained by this procedure is further denominated as p0130.

In a following step, the nptII selectable marker gene was removed from p0130 by digestion with BamHI and subsequent religation of the compatible vector overhangs. This procedure yielded a binary T-DNA vector denominated as pCDVIB. The vector pCDVIB thus contains an octopine-type LB region spanning a core sequence flanked by a border outer region and thus is a construct of the B-type as indicated in FIG. 2.

To create a construct of the E-type indicated in FIG. 2, two long oligonucleotides, prmCDVIB1F and prmCDVIB1R, were designed with the following sequences:

prmCDVIB1F: 5'(1)CATGGAGCGGCGGCAG-GATATATTCAATTGTAAATGGCTAGCG-GCGGCAGG ATATATTCAATTGTAAATGGCTG (84)3' (SEQ ID NO 5); partial NcoI-site in bold and double underlined, left border core sequences in italics and single underlined, 3' end G residue part of a BamHI-site; and prmCDVIB1R 5'(1)GATCCSGCCSTTTSCSST-TGSSTSTSTCCTGCCGCCGCTAGCCATT-TACAATT GAATTATATCCTGCCGCCGCTC(84)3' (SEQ ID NO 6); partial BamHI-site in bold and double underlined, left border core sequences in italics and single underlined, 3' end C residue part of a NcoI-site.

The oligonucleotides prmCDVIB1F and prmCDVIB1R are complementary over a distance of 80 nucleotides and yield, after annealing, a dsDNA fragment with at its 5' (relative to prmCDVIB1F) a 5' NcoI overhang ('CATG') and at its 3' (relative to prmCDVIB1F) a 5' BamHI overhang ('GATC'). Said dsDNA fragment furthermore contains a tandem of two octopine-type LB core sequences corresponding to nucleotides 12-33 and 46-67 of prmCDVIB1F. Both LB core sequences are extended upstream and downstream by a further 6 basepairs originating from the natural LB of pTi15955 and identical as in pTiAch5 (Gielen et al. 1984). The repeats in the tandem of LB core sequences are thus separated by 12 bp. Said dsDNA fragment with the tandemly arranged LB core sequences was inserted upstream of and adjacent to the LB core sequence of p0130 digested with NcoI and BamHI, yielding pCDVIB1.

pCDVIB1 thus contains an octopine-type left border region spanning a LB outer region and three tandemly arranged LB core sequences.

To create a construct of the A-type indicated in FIG. 2, two long oligonucleotides, prmCDVIB2F and prmCDVIB2R, were designed with the following sequences:

prmCDVIB2F: 5'(1)CATGGCCGGGAAATCTACATG-GATCAGCAATGAGTATGATGGTCAATATGGA GAAAAAGAAAGAGTAATTAC-CAATTTTTTTTCAATTCAAAAATGTA-GATGTCCG(116) 3'(SEQ ID NO 7); partial NcoI-site in bold and double underlined, 3' end G residue part of a BamHI-site; and pCDVIB2R: 5'(1) GATCCGGACATCTA-CATTTTTGAATTGAAAAAAAATTGG-TAATTACTCTTTCTT TTTCTCCATATTGACCAT-CATACTCATTGCTGATCCATGTAGATTTCCCGGC (116)3'(SEQ ID NO 8); partial BamHI-site in bold and double underlined, 3' end C residue part of a NcoI-site.

The oligonucleotides prmCDVIB2F and prmCDVIB2R are complementary over a distance of 112 nucleotides and yield, after annealing, a dsDNA fragment with at its 5' (relative to prmCDVIB1F) a 5' NcoI overhang ('CATG') and at its 3' (relative to prmCDVIB1F) a 5' BamHI overhang ('GATC'). Said dsDNA fragment furthermore contains a 112 bp inner region of pTi15955. This fragment was inserted upstream of and adjacent to the LB core sequence of p0130 digested with NcoI and BamHI, yielding pCDVIB2. PCDVIB2 thus contains an octopine-type LB region spanning a LB core sequence embedded in LB outer and inner regions.

Another T-DNA vector construct was made with a modified LB combining features of E- and F-type constructs indicated in FIG. 2. An integral nopaline-type LB region was obtained as a 331 bp BclI-EcoRI fragment of binary T-DNA vector pPZP200. This fragment spans nopaline-type LB outer region, LB core sequence and LB inner region originating from pTiC58 (Gielen et al. 1999). Said nopaline-type LB region was inserted upstream of and adjacent to the octopine-type LB region of pCDVIB2 (containing tandemly repeated octopine-type LB core sequences) digested with BamHI (located at the 3' of the LB core sequence tandem, relative to prmCDVIB2F) and EcoRI, yielding pCDVIB3. PCDVIB3 thus contains a LB region spanning a copy of an integral octopine-type LB region with three tandemly arranged core sequences and a copy of an integral nopaline-type LB region.

All described exemplary T-DNA vectors with a modified LB region, i.e. pCDVIB, pCDVIB1, pCDVIB2 and pCDVIB3 serve as a starting point to insert gene(s) of interest and/or selectable marker gene(s) in between RB and LB of said T-DNA vectors.

The neomycin phosphotransferase (nptII) selectable marker gene under control of the nopaline synthase (nos) promoter (Pnos-nptII-3'ocs) and the β-glucuronidase (gus) expression cassette under control of the 35S cauliflower mosaic virus promoter (P35S-gus-3'nos) were inserted between the RB and LB of said T-DNA vectors.

The nptII-gus cassette was derived from the pXD610 plasmid (De Loose et al., 1995) as an EcoRI-AgeI fragment. This fragment was inserted into the SalI/EcoRI sites of pCDVIB; pCDVIB1; pCDVIB2 and pCDVIB3. To obtain compatible sticky ends, two adaptor oligonucleotides between the open AgeI- and SalI-site were used with the following sequences:

Napod3: CCGGTGGCTCGAGG (SEQ ID NO 9); partial AgeI-site in bold, 3' end G residue part of a SalI-site and Napod4: TCGACCTCGAGCCA (SEQ ID NO 10); partial SalI underlined, 3' end A residue part of a AgeI-site The oligonucleotides Napod3 and Napod4 are complementary over a distance of 8 nucleotides and yield, after annealing, a dsDNA fragment with at its 5' (relative to Napod3) a 5' AgeI overhang ('CCGG') and at its 3' (relative to Napod3) a SalI overhang ('TCGA'). The obtained vectors were called pCDVIB+gusnpt, pCDVIB1+gusnpt, pCDVIB2+gusnpt, pCDVIB3+gusnpt.

Example 5

Construction of Optimized T-DNA Vectors with Integrated Recombination Sites.

Figure 3:
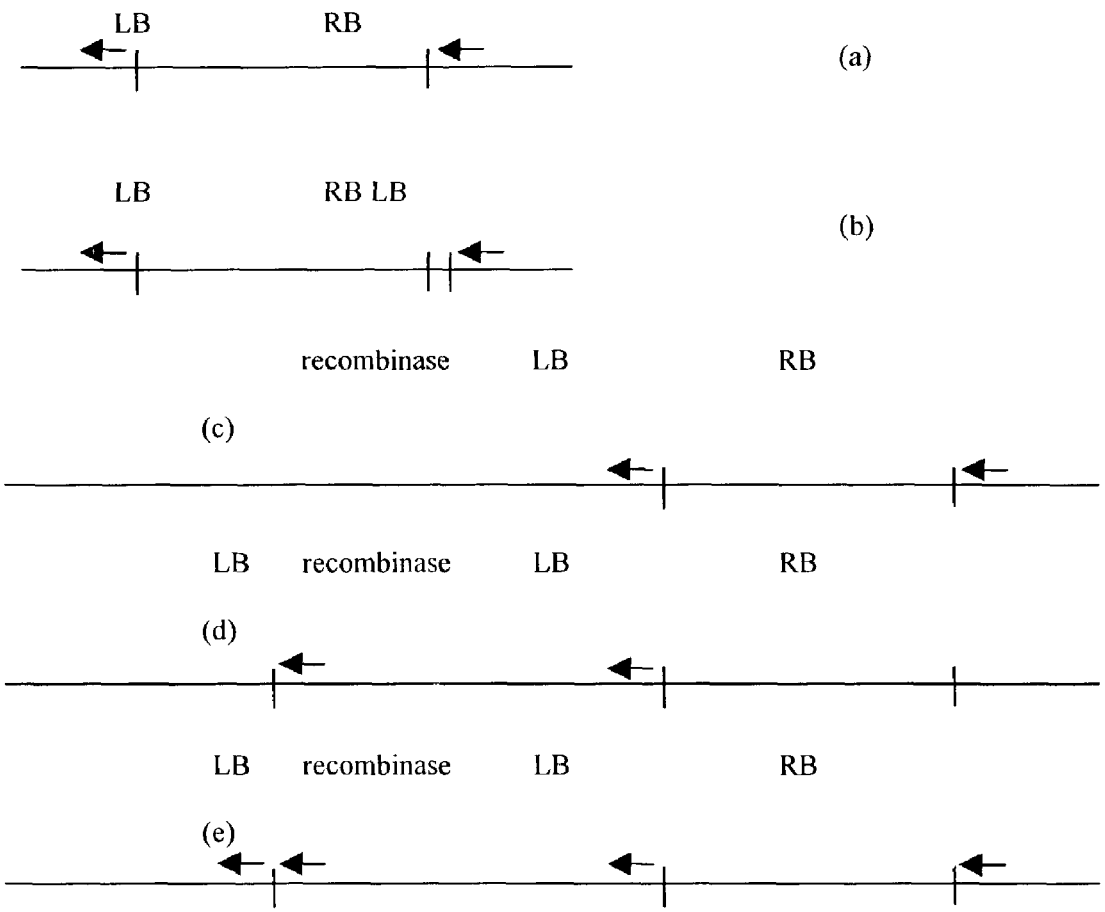
FIG. 3. Schematic representation of T-DNA constructs designed to allow curing of vector backbone sequences integrated in the genome of a eukaryote. LB: left border; RB: right border.
Figure 4:
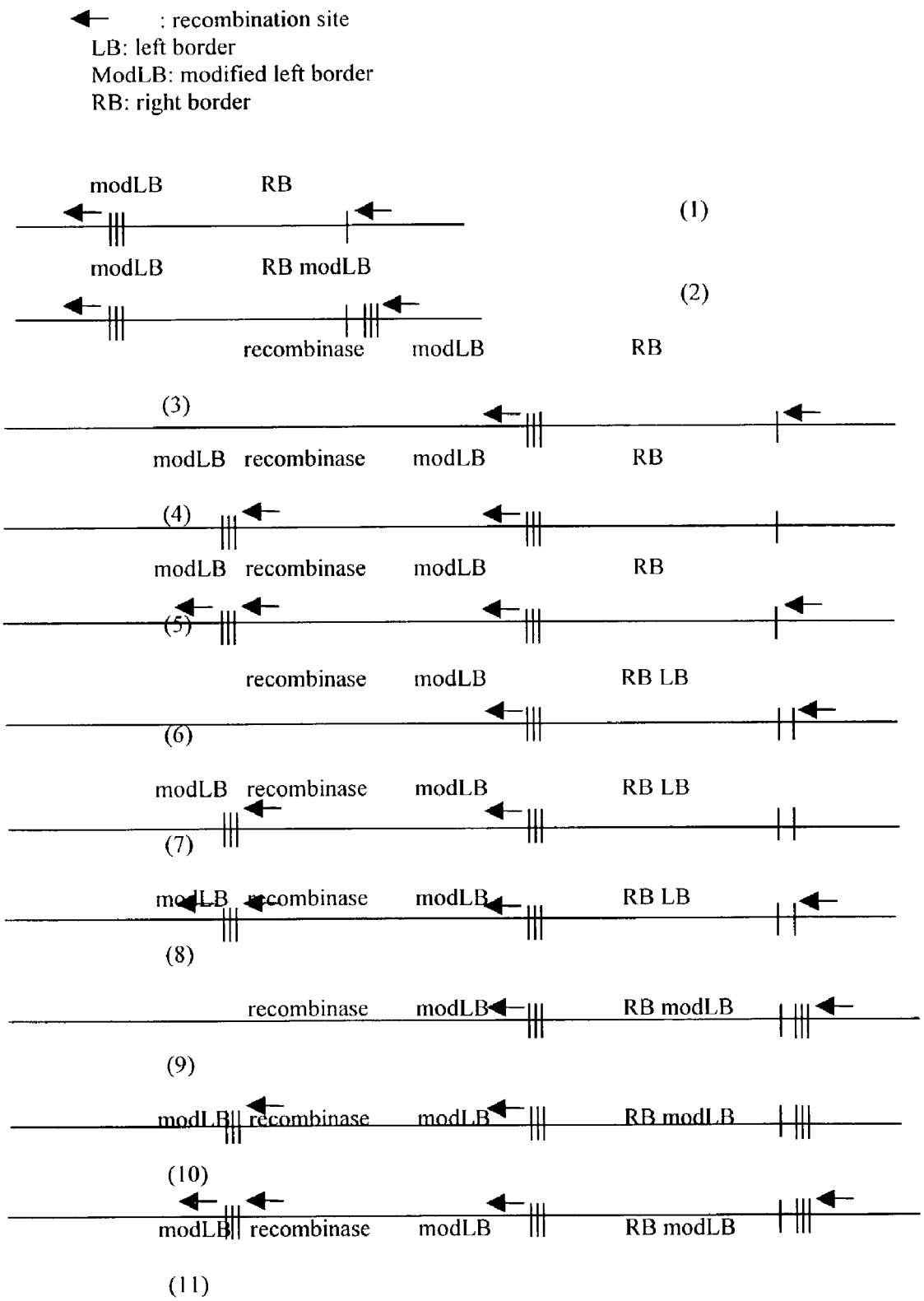
FIG. 4. Schematic representation of exemplary T-DNA constructs featuring combinations of modifications according to the current invention. LB: left border; RB: right border; modLB: modified left border (see FIG. 2 for possible modifications).

Exemplary optimized binary T-DNA vectors of the types indicated in FIG. 3 are constructed as follows. In this example, the optimized binary T-DNA vector is derived from pCDVIB (see Example 4).

One strategy to introduce recombination sites comprises:

1. Designing pairs of primers for PCR amplification of vector domains upstream of the RB and downstream of the LB. Said domains are to encompass a unique restriction site upstream of the RB (e.g. the NarI-site in the pVS1 replicon contained within the pCDVIB vector backbone) and downstream of the LB (e.g. the BclI-site in the Sm/Sp resistance marker contained within the pCDVIB vector backbone). The PCR primers located at or close to the RB or LB are designed such that they contain a 5' unique restriction site followed by the recombination site (e.g. the FRT site) in its right orientation (as direct repeats outside the T-DNA borders in case of FRT sites) and followed by part of the border outer regions. The obtained PCR products are subsequently digested with the appropriate enzymes.

2. Designing complementary oligonucleotide pairs (similar as in Example 4) after annealing yielding dsDNA molecules spanning either the RB or LB core sequence and with one overhang complementary to the 5' unique restriction site of said primers in (1) located at or close to the borders and with a second overhang complementary to a unique restriction site downstream of the RB core sequence (e.g. ScaI in pCDVIB) or complementary to a unique restriction site upstream of the LB core sequence (e.g. NcoI in PCDVIB).

3. (a) Digesting pCDVIB with NarI (in the pVS replicon) and ScaI (downstream of RB core sequence) followed by a trimolecular ligation of 1) the resulting vector with 2) the digested PCR product encompassing the deleted pCDVIB fragment and introducing the recombination sites and 3) the dsDNA based on the annealed oligonucleotides and reintroducing the RB core sequence.

(b) Digesting the vector finally obtained in (3a) with BclI (in Sm/Sp resistance marker) and NcoI (upstream of LB core sequence) followed by a trimolecular ligation of 1) the resulting vector with 2) the digested PCR product encompassing the deleted pCDVIB fragment and introducing the recombination sites and 3) the dsDNA based on the annealed oligonucleotides and reintroducing the LB core sequence.

The described exemplary T-DNA vectors with introduced recombination sites serves as a starting point to insert gene(s) of interest and/or selectable marker gene(s) in between RB and LB of said T-DNA vector.

Example 6

Prediction of Vector Backbone Transfer Frequencies Using Induced *Agrobacterium* Cultures.

*Agrobacterium* strains containing any T-DNA vector can be induced for production of ssT-DNA strands by adding acetosyringone at a concentration of 100 μM to the culture medium (Durrenberger et al. 1989). The production of ssT-DNA strands can be analyzed using either one of the following methods (see included figure for schematic overview).

1. Total DNA is isolated from the *Agrobacterium* cells containing a given T-DNA vector. Duplicate non-denaturing Southern blots (Tinland et al. 1995) of about 5 μg of this DNA isolated from the different *Agrobacterium* strains are hybridized to two different probes: one recognizing a DNA sequence that is part of the T-DNA and one recognizing a DNA sequence that is part of the vector backbone flanking the left border. The hybridization signal of the probe recognizing the vector backbone sequences is absent or much reduced in the case of a T-DNA vector from which the left border is processed with high efficiency. The hybridization signal of the probe recognizing the T-DNA is, however, be constant.

2. Total DNA is isolated from the *Agrobacterium* cells containing a given T-DNA vector. Two separate digests containing equal amounts of total DNA are set up, one with a restriction enzyme cuffing the T-DNA at or very near to the left border, the other one with a restriction enzyme cutting within the T-DNA sequence. The ssT-DNA strands will, however, remain intact. Specific primer pairs are used in a quantitative PCR to amplify a T-DNA-borne sequence and a vector-borne sequence downstream of the left border. Again, no or much less vector backbone amplification product is obtained in the case of a T-DNA vector from which the left border is processed with high efficiency. The amounts of T-DNA-specific amplification product is, however, constant.

For both types of analyses, an additional GFP (green fluorescent protein) expression cassette is cloned immediately downstream of the left border of the different T-DNA vectors. This cassette provides a fully known 'vector backbone' sequence downstream of the left border. The GUS expression cassette is used as T-DNA-specific target. Both expression cassettes contain an intron in the GFP- and GUS-coding regions, respectively, to prevent expression of both markers in Agrobacterium.

In FIG. 6 both experimental setups are schematically drawn. Above the solid black line indicating the T-DNA vector, the hybridization approach is shown and below the solid line, the quantitative PCR approach is shown.

Example 7

Early Analysis of Vector Backbone Transfer Sequences to Plant Cells.

The constructs outlined in Example 6 and containing an additional GFP expression cassette downstream of the left border are used in a transient expression assay for assessment of vector backbone transfer to plant cells. To this end, Arabidopsis root fragments are transformed with Agrobacterium (De Buck et al. 1999, Valvekens et al. 1988) containing a T-DNA vector modified according to the invention. After 3 days of co-cultivation, roots are assessed first for transient expression of the GFP followed by assessment of transiently expressed GUS. The level of GFP expression is low or zero in the case of a T-DNA vector from which the left border is processed with high efficiency. The levels of GUS activities are, however, constant.

Alternatively, the procedure of reverse transcription followed by PCR is followed for detecting and quantitating the levels of transiently accumulated GFP- and GUS-transcripts (Narasimhulu et al. 1996). Again,. no or much less GFP-specific amplification product is obtained in the case of a T-DNA vector from which the left border is processed with high efficiency. The amounts of GUS-specific amplification product is, however, constant.

Example 8

Curing Transformed Plants of Integrated Vector Backbone Sequences.

Plants (e.g. Arabidopsis) are transformed (see Example 1) with the exemplary T-DNA vector of Example 5 containing the FRT recombination sites. Regenerated plants are tested for vector backbone integration according to any of the methods described in Examples 2-3 or 6-7 and transgenic plants containing the T-DNA and vector backbone in their genome are selected.

At flowering, one set of selected transgenic plants are cross-pollinated with pollen derived from another transgenic plant constitutively expressing the FLP site-specific recombinase while a second set of selected transgenic plants are cross-pollinated with pollen derived from a wild-type plant. Seeds are collected and sown on medium containing a selective agent. Surviving plants (due to the selectable marker in the T-DNA) of both crossings are analyzed again for the presence of T-DNA and for the presence of vector backbone. In a substantial part of the progeny of the crossings involving the FLP-expressing parent and containing the T-DNA, the vector backbone sequences are removed. In the progeny of the crossings involving the wild-type parent and containing the T-DNA, the vector backbone sequences are still present.

Example 9

Cloning of the virD Locus and Influence of an Extra Copy of the Locus on Vector Backbone Transfer.

The sequences of the octopine-type and nopaline-type virD loci are known (Yanofsky et al. 1986, Jayaswal et al. 1987; and Wang et al. 1990, respectively). Specific primers are designed enabling PCR amplification of the complete virD loci. These loci are subsequently subcloned in a plasmid carrying the P15a replicon (Chang and Cohen 1987) and a tetracyclin resistance marker derived from pAlter (Promega). The plasmids are subsequently mobilized to Agrobacterium containing a T-DNA vector. Transfer of vector backbone sequences by said Agrobacterium strains is analyzed according to any of the methods described in Examples 2, 3, 5 or 6.

Example 10

Determination of the Frequency of Initiation of Transfer at the Left Border

Plants are transformed with the T-DNA vectors described in FIG. 2. Total DNA is prepared and three primer sets are synthesized to perform different PCR reactions. The first primer set amplifies an internal T-DNA fragment, adjacent to the left border repeat (PCR fragment 1). The second primer set amplifies a T-DNA/vector fragment spanning the T-DNA left border region and the vector region adjacent to the left border repeat (PCR fragment 2). Finally, the third primer set amplifies a vector fragment adjacent to the left border repeat (PCR fragment 3). Dependent on whether the vector transfer results from readthrough at the left border or initiation at the left border, different PCR fragments are amplified. When only PCR fragment 1 is present, the T-DNA transfer started at the right border and stopped at the left border and no vector DNA was transferred. When PCR fragments 1,2 and 3 are present, the T-DNA transfer started at the right border but didn't stop at the left border. When PCR fragments 1 and 3 are present but not fragment 2, the vector transfer started at the left border, independently of T-DNA transfer from the right border. Performing these different PCR reactions for approximately 50 transformants thus yields the frequency of readthrough at the left border and the frequency of initiation at the left border repeat. The frequency of readthrough and initiation of vector transfer is determined for the different T-DNA vectors with the left border repeat in different contexts.

Table 1. Presence (+) or absence (−) of vector sequences linked to the LB and RB of the T-DNA in the transgenic A. thaliana plants co-transformed with both K and Hsb T-DNA vectors.

TABLE 1

Presence (+) or absence (−) of vector sequences linked to the LB and RB of the T-DNA in the transgenic *A. thaliana* plants co-transformed with both K and Hsb T-DNA vectors.

| Number of co-transformants[a] Series1 (18 plants) | LB100 | LB1000 | RB100 | RB1000 | LB100 | LB1000 | RB100 | RB1000 | PicA | Unl[b] |
|---|---|---|---|---|---|---|---|---|---|---|
| | | K | | | | Hsb | | | | |
| 3 | − | − | − | − | − | − | − | − | − | − |
| 1 | − | − | − | − | − | − | − | − | − | +(R) |
| 1 | − | − | − | − | + | − | − | − | − | +(R) |
| 3 | − | − | − | − | + | + | − | − | − | +(R) |
| 1 | − | − | − | − | + | + | − | − | − | − |
| 1 | + | + | − | − | − | − | − | − | − | − |
| 1 | − | − | − | − | + | − | + | + | − | nt[c] |
| 1 | + | + | − | − | + | − | + | − | − | nt |
| 2 | − | − | − | − | + | + | + | + | − | nt |
| 1 | + | + | + | − | − | − | − | − | − | nt |
| 1 | + | + | + | + | − | − | − | − | − | nt |
| 1 | + | + | + | + | + | + | − | − | − | nt |
| 1 | + | + | + | + | + | + | + | + | − | nt |

[a] Indicates the number of transformants with a particular pattern of vector sequences present in the transformed plants.
[b] Right (R) or left (L) external border repeat fragments are present of either of the T-DNA vectors, not linked to either of the borders.
[c] Not tested

[a] Indices the number of transformants with a particular pattern of vector sequences present in the transformed plants.

[b] Right (R) or left (L) external border repeat fragments are present of either of the T-DNA vectors, not linked to either of the borders.

[c.] Not tested

Table 2. Presence (+) or absence (−) of vector sequences to the LB and RB of the T-DNA in the transgenic *N. tabacum* plants transformed with the Ksb T-DNA vector.

TABLE 2

Presence (+) or absence (−) of vector sequences linked to the LB and RB of the T-DNA in the transgenic *N. tabacum* plants transformed with the Ksb T-DNA vector.

| Number of co-transformants[a] Series2 (36 plants) | LB100 | LB1000 | RB100 | RB1000 | PicA | Unl[b] |
|---|---|---|---|---|---|---|
| | | Ksb | | | | |
| 17 | − | − | − | − | − | − |
| 3 | + | − | − | − | − | − |
| 2 | + | + | − | − | − | +(R) |
| 3 | + | + | − | − | − | − |
| 1 | − | − | + | + | − | − |
| 1 | + | − | + | − | − | nt[c] |
| 1 | + | + | + | − | − | nt |
| 8 | + | + | + | + | − | nt |

[a] Indicates the number of transformants with a particular pattern of vector sequences present in the transformed plants.
[b] Right (R) or left (L) external border repeat fragments are present of either of the T-DNA vectors, not linked to either of the borders.
[c] Not tested

[a] Indicates the number of transformants with a particular pattern of vector sequences present in the transformed plants.

[b] Right (R) or left (L) external border repeat fragments are present of either of the T-DNA vectors, not linked to either of the borders.

[c.] Not tested

References

EP0332104 Montoya, A., Duesing, J., Harms, C., Meins, F., Payne, G., Ryals, J. and Sperisen, C. 1989. Chemically regulatable DNA sequences and genes and uses thereof.

EP0823480 Gaelweiler, L., Palme, K., Grosskopf-Kroiler, D., Schell, J. and Moore, I. 1998. Controlled gene expression in plants.

U.S. Pat. No. 5,527,695 Hodges T. K. and Lyznik L. 1996. Controlled modification of eukaryotic genomes.

U.S. Pat. No. 5,801,027 Ramsay, N., Bennett, M. and May, S. 1998. Method of using transactivation proteins to control gene expression in transgenic plants.

WO90/08826 Bright, S. W. J., Greenland, A. J., Schuch, W. W. and Bridges, I. G. 1990. Gene switch.

WO97/12046 Hansen, G. and Chilton, M. -D. 1997. Improved integration of exogenous DNA delivered to eukaryotic cells.

WO97/30164 Haseloff, J. P. and Hodge, S. 1997. Improvements in or relating to gene expression.

WO98/45455 Beijersbergen, A. G., de Groot, M. J. A., Gouka, R. J., Hooykaas, P. J. and Bundock, P. 1998. *Agrobacterium*-mediated transformation of moulds, in particular those belonging to the genus Aspergillus.

WO98/59062 Liu, Z. -B. and Odell, J. T. 1998. Specific gene activation by chimeric GAL4 transcription factors in stable transgenic plants.

WO99/01563 Stuiver, M. H., Ponstein, A. S., Ohl, S. A., Goddijn, O. J. M., Simons, L. H., Dekker, B. M. M., Hoekstra, S. and Tigelaar, H. 1999. Plasmids for plant transformation and method for using the same.

WO99/14348 Lefebvre, D., Ko, K., Ko, Z. and Tremblay, L. 1999. In planta transformation of plants.

WO99/23202 Ow, D., and Srivastava, V. 1999. Resolution of complex integration patterns to obtain single copy transgenes.

WO99/25821 Baszczynski, C. L., Bowen, B. A., Peterson, D. J. and Tagliani, L. A. 1999. Compositions and methods for genetic modification of plants.

WO99/25840 Baszczynski C. L., Lyznik L., Gordon-Kamm W. J., Rao A. G., Tagliani, L. A. and Guan, X. 1999. A novel method for the integration of foreign DNA into eukaryotic genomes.

Bundock, P., den Dulk-Ras, A., Beijersbergen, A. and Hooykaas, P. J. 1995. Trans-kingdom T-DNA transfer from *Agrobacterium tumefaciens* to *Saccharomyces cerevisiae*. EMBO J 14: 3206-3214.

Caplan, A. B., Van Montagu, M. and Schell, J. 1985. Genetic analysis of integration mediated by single T-DNA borders. J Bacteriol 161, 655-664.

Chang, A. C. and Cohen, S. N. 1987. Construction and characterization of amplifiable multicopy DNA cloning vehicles derived from the P15A cryptic miniplasmid. J Bacteriol 134: 1141-1156.

Clough, S. J. and Bent, A. F. 1998. Floral dip: a simplified method for *Agrobacterium*-mediated transformation of *Arabidopsis thaliana*. Plant J 16: 735-743.

Cluster, P. D., O'Dell, M., Metzlaff, M. and Flavell, R. B. 1996. Details of T-DNA structural organization from a transgenic Petunia population exhibiting co-suppression. Plant Mol Biol 32: 1197-1203.

Dale, E. C. and Ow, D. W. 1990. Intra- and intermolecular site-specific recombination in plant cells mediated by bacteriophage P1 recombinase. Gene 91: 79-85.

De Buck, S., Jacobs, A., Van Montagu, M. and Depicker, A. 1998. *Agrobacterium tumefaciens* transformation and cotransformation frequencies of *Arabidopsis thaliana* root explants and tobacco protoplasts. Mol Plant-Microbe Interact 11: 449-457.

De Buck, S., Jacobs, A., Van Montagu, M. and Depicker, A. 1999. The DNA sequences of T-DNA junctions suggest that complex T-DNA loci are formed by a recombination process resembling T-DNA integration. Plant J (in press)

de Groot, M. J., Bundock, P., Hooykaas, P. J. and Beijersbergen, A. G. 1998. *Agrobacterium tumefaciens*-mediated transformation of filamentous fungi. Nat Biotechnol 16: 839-842.

De Neve, M., De Buck, S., Jacobs, A., Van Montagu, M. and Depicker A. 1997. T-DNA integration patterns in co-transformed plant cells suggest that T-DNA repeats originate from ligation of separate T-DNAs. Plant J 11: 15-29.

Deng, W., Chen, L., Peng, W. T., Liang, X., Sekiguchi, S., Gordon, M. P., Comai, L. and Nester, E. W. 1999. VirE1 is a specific molecular chaperone for the exported single-stranded-DNA-binding protein VirE2 in *Agrobacterium*. Mol Microbiol 31: 1795-1807.

Durrenberger, F., Crameri, A., Hohn, B. and Koukolikova-Nicola, Z. 1989. Covalently bound VirD2 protein of *Agrobacterium tumefaciens* protects the T-DNA from exonucleolytic degradation. Proc Natl Acad Sci USA 86: 9154-9158.

Errampali, D., Patton, D., Castle, L., Mickelson, K., Hansen, K., Schnall, J., Feldmann, K. and Meinke, D. 1991. Embyrogenic lethals and T-DNA insertional mutagenesis in *Arabidopsis*. Plant Cell 3: 149-157.

Fedoroff, N. V. and Smith, D. L. 1993. A versatile system for detecting transposition in *Arabidopsis*. Plant J 3: 273-289.

Feldmann, K. A. 1991. T-DNA insertion mutagenesis in *Arabidopsis*: a mutational spectrum. Plant J 1:71-82.

Gelvin, S. B. 1998a. The introduction and expression of transgenes in plants. Curr Opin Biotechnol 9: 227-232.

Gelvin, S. B. 1998b. *Agrobacterium* VirE2 proteins can form a complex with T strands in the plant cytoplasm. J Bacteriol 180: 4300-4302.

Ghai, J. and Das, A. 1989. The virD operon of *Agrobacterium tumefaciens* Ti plasmid encodes a DNA-relaxing enzyme. Proc Natl Acad Sci USA 86: 3109-3113.

Gheysen, G., Angenon, G. and Van Montagu, M. 1998. *Agrobacterium*-mediated plant transformation: a scientifically intriguing story with significant applications. In K. Lindsey (Ed.), Transgenic Plant Research. Harwood Academic Publishers, Amsterdam, pp. 1-33.

Gielen, J., De Beuckeleer, M., Seurinck, J., Deboeckl, F., De Greve, H., Lemmers, M., Van Montagu, M. and Schell, J. 1984. The complete nucleotide sequence of the TL-DNA of the *Agrobacterium tumefaciens* plasmid pTiAch5. EMBO J 3: 835-846.

Gielen, J., Terryn, N., Villaroel, R. and Van Montagu, M. 1999. Complete nucleotide sequence of the T-DNA region of the plant tumour-inducing *Agrobacterium tumefaciens* Ti plasmid pTiC58. J Exper Bot 50: 1421-1422.

Gouka, R. J., Gerk, C., Hooykaas, P. J., Bundock, P., Musters, W., Verrips, C. T. and de Groot, M. J. 1999. Transformation of *Aspergillus awamori* by *Agrobacterium tumefaciens*-mediated homologous recombination. Nat Biotechnol 17, 598-601.

Guralnick, B., Thomsen, G. and Citovsky, V. 1996. Transport of DNA into the nuclei of *Xenopus oocytes* by a modified VirE2 protein of *Agrobacterium*. Plant Cell 8: 363-373.

Hansen, G. and Chilton, M. -D. 1996. 'Agrolistic' transformation of plant cells: integration of T-strands generated in planta. Proc Natl Acad Sci USA 93: 14978-14983.

Hansen, G., Shilito, R. D. and Chilton, M. -D. 1997. T-strand integration in maize protoplasts after codelivery of a T-DNA substrate and virulence genes. Proc Natl Acad Sci USA 94:11726-11730. Hanson, B., Engler, D., Moy, Y., Newman, B., Ralston, E. and Gutterson, N. 1999. A simple method to enrich an *Agrobacterium*-transformed population for plants containing only T-DNA sequences. Plant J 19: 727-734.

Horsch, R. B., Fry, J. E., Hoffmann, N. L., Eichholtz, D., Rogers, S. G. and Fraley, R. T. 1985. A simple and general method for transferring genes into plants. Science 227: 1229-1231.

Horsch, R. B. and Klee, H. J. 1986. Rapid assay of foreign gene expression in leaf discs transformed by *Agrobacterium tumefaciens*: role of T-DNA borders in the transfer process. Proc Natl Acad Sci USA 83: 4428-4432.

Iglesias, V. Moscone, E. A., Papp, I., Neuhuber, F., Michalowski, S., Phelan, T., Spiker, S. Matzke, M. and Matzke, A. J. M. 1997. Molecular and cytogenetic analyses of stably and unstably expressed transgene loci in tobacco. Plant Cell 9: 1251-1264.

Jayaswal, R. K., Veluthambi, K., Gelvin, S. B. and Slightom, J. L. 1987. Double-stranded cleavage of T-DNA and generation of single-stranded T-DNA molecules in *Escherichia coli* by a virD-encoded border-specific endonuclease from *Agrobacterium tumefaciens*. J Bacteriol 169: 5035-5045.

Jakowitsch, J., Papp, I., Moscone, E. A., van der Winden, J., Matzke, M. and Matzke, A. J. M. 1999. Molecular and cytogenetic characterization of a transgene locus that induces silencing and methylation of homologous promoters in trans. Plant J 17: 131-140.

Jen, G. C. and Chilton, M. D. 1986a. Activity of T-DNA borders in plant cell transformation by mini-T plasmids. J Bacteriol 166: 491-499.

Jen, G. C. and Chilton, M. D. 1986b. The right border region of pTiT37 T-DNA is intrinsically more active than the left border region in promoting T-DNA transformation. Proc Natl Acad Sci USA 83: 3895-3899.

Jones, J. D. G., Dunsmuir, P., and Bedbrook, J. (1985). High level expression of introduced chimaeric genes in regenerated transformed plants. EMBO J. 4, 2411-2418.

Koncz, C., Nemeth, K., Redei, G. P. and Schell, J. 1992. T-DNA insertional mutagenesis in *Arabidopsis*. Plant Mol. Biol 20: 963-976.

Kononov, M. E., Bassuner, B. and Gelvin, S. B. 1997. Integration of T-DNA binary vector 'backbone' sequences into the tobacco genome: evidence for multiple complex patterns of integration. Plant J 11: 945-957.

Maniatis, T., Fritsch, E. F. and Sambrook, J. 1982. Molecular Cloning: A Laboratory Manual. Cold Spring Harbor Laboratory, Cold Spring Harbor.

Martineau, B., Voelker, T. A. and Sanders, R. A. 1994. On defining T-DNA. Plant Cell 6: 1032-1033 (Letter to the editor).

Matzke, A. J. M. and Matzke, M. A. 1998. Position effects and epigenetic silencing of plant transgenes. Curr Opin Plant Biol 1: 142-148.

Mysore, K. S., Bassuner, B., Deng, X. B., Darbinian, N. S., Motchoulski, A., Ream, W. and Gelvin, S. B. 1998. Role of the *Agrobacterium tumefaciens* VirD2 protein in T-DNA transfer and integration. Mol Plant Microbe Interact 11: 668-683.

Narasimhulu, S. B., Deng, X. B., Sarria, R. and Gelvin, S. B. 1996. Early transcription of *Agrobacterium* T-DNA genes in tobacco and maize. Plant Cell 8: 873-886.

Onouichi, H., Nishihama, R., Kudo, M., Machida, Y., and Machida, C. (1995). Visualization of site-specific recombination catalyzed by a recombinase from *Zygosaccharomyces rouxii* in *Arabidopsis thaliana*. Mol. Gen. Genet. 247, 653-660.

Onouchi, H., Yokoi, K., Machida, C., Matsuzaki, H., Oshima, Y., Matsuoka, K., Nakamura, K., and Machida, Y. (1991). Operation of an efficient site-specific recombination system of *Zygosaccharomyces rouxii* in tobacco cells. Nucleic Acids Res. 19, 6373-6378.

Ooms, G., Bakker, A., Molendijk, L., Wullems, G. J., Gordon, M. P., Nester, E. W. and Schilperoort, R. A. 1982. T-DNA organization in homogeneous and heterogeneous octopine-type crown gall tissues of Nicotiana tabacum. Cell 30: 589-597.

Osborne, B. I., Wirtz, U. and Baker, B. 1995. A system for insertional mutagenesis and chromosomal rearrangement using the Ds transposon and Cre-lox. Plant J 7: 687-701.

Pansegrau, W. and Lanka, E. 1996. Mechanisms of intitiation and termination reactions in conjugative DNA processing. J Biol Chem 271: 13068-13076.

Peralta, E. G., Hellmiss, R. and Ream, W. 1986. Overdrive, a T-DNA transmission enhancer on the A. tumefaciens tumour-inducing plasmid. EMBO J 5, 1137-1142.

Ramanathan, V. and Veluthambi, K. 1995. Transfer of non-T-DNA portions of the *Agrobacterium tumefaciens* Ti plasmid pTiA6 from the left terminus of $T_L$-DNA. Plant Mol Biol 28: 1149-1154.

Relic, B., Andjelkovic, M., Rossi, L., Nagamine, Y. and Hohn, B. 1998. Interaction of the DNA modifying proteins VirD1 and VirD2 of *Agrobacterium tumefaciens*: analysis by subcellular localization in mammalian cells. Proc Natl Acad Sci USA 95: 9105-9110.

Rossi, L., Hohn, B. and Tinland, B. 1993. The VirD2 protein of *Agrobacterium tumefaciens* carries nuclear localization signals important for transfer of T-DNA to plant. Mol Gen Genet 239: 345-353.

Rossi, L., Hohn, B. and Tinland, B. 1996. Integration of complete transferred DNA units is dependent on the activity of virulence E2 protein of *Agrobacterium tumefaciens*. Proc Natl Acad Sci USA 93: 126-130.

Schlappi, M., Smith, D. and Fedoroff, N. 1993. TnpA transactivates methylated maize Suppressor-mutator transposable elements in transgenic tobacco. Genetics 133: 1009-1021.

Shaw, C. H., Watson, M. D., Carter, G. H. and Shaw, C. H. 1984. The right hand copy of the nopaline Ti-plasmid 25 bp repeat is required for tumour formation. Nucleic Acids Res 12: 6031-6041.

Shurvinton, C. E., Hodges, L., Ream, W. 1992. A nuclear localization signal and the C-terminal omega sequence in the *Agrobacterium tumefaciens* VirD2 endonuclease are important for tumor formation. Proc Natl Acad Sci USA 89: 11837-11841.

Sugita, K., Kasahara, T., Matsunaga, E., and Ebinuma, H. (2000). Technical advance: A transformation vector for the production of marker-free transgenic plants containing a single copy transgene at high frequency [In Process Citation]. Plant J. 22, 461-469.

Tinland, B., Schoumacher, F., Gloeckler, V., Bravo-Angel, A. M. and Hohn, B. 1995. The *Agrobacterium tumefaciens* virulence D2 protein is responsible for precise integration of T-DNA into the plant genome. EMBO J 14: 3585-3595.

Valvekens, D., Van Montagu, D. and Van Lijsebettens, M. 1988. *Agrobacterium tumefaciens*-mediated transformation of *Arabidopsis thaliana* root explants by using kanamycin selection. Proc Natl Acad Sci USA 85: 5536-5540.

van der Graaff, E., den Dulk-Ras, A. and Hooykaas, P. J. J. 1996. Deviating T-DNA transfer from *Agrobacterium tumefaciens* to plants. Plant Mol Biol 31: 677-681.

van Haaren, M. J. J., Sedee, N. J. A., Schilperoort, R. A. and Hooykaas, P. J. J. 1987. Overdrive is a T-region transfer enhancer which stimulates T-strand production in *Agrobacterium tumefaciens*. Nucl Acids Res 15: 8983-8997.

Van Lijsebettens, M., Vanderhaegen, R., and Van Montagu, M. 1991. Insertional mutagenesis in *Arabidopsis thaliana*: isolation of a T-DNA-linked mutation that alters leaf morphology. Theor Appl Genet 81: 277-284.

Van Sluys, M. A., Tempe, J. and Fedoroff, N. 1987. Studies on the introduction and mobility of the maize Activator element in *Arabidopsis thaliana* and *Daucus carota*. EMBO J 6: 3881-3889.

Virts, E. L. and Gelvin, S. B. 1985. Analysis of transfer of tumor-inducing plasmids from *Agrobacterium tumefaciens* to *Petunia protoplasts*. J. Bacteriol 162: 1030-1038.

Wang, K., Genetello, C., Van Montagu, M. and Zambryski, P. C. 1987. Sequence context of the T-DNA border repeat element determines its relative activity during T-DNA transfer to plant cells. Mol Gen Genet 210: 338-346.

Wang, K., Herrera-Estrella, A. and Van Montagu, M. 1990. Overexpression of virD1 and virD2 genes in *Agrobacterium tumefaciens* enhances T-complex formation and plant transformation. J Bacteriol 172: 4432-4440.

Waters, V. L. and Guiney, D. G. 1993. Processes at the nick region link conjugation, T-DNA transfer and rolling circle replication. Mol Microbiol 9: 1123-1130.

Wenck, A., Czakó, M., Kanevski, I. and Márton, L. 1997. Frequent collinear long transfer of DNA inclusive of the whole binary vector during *Agrobacterium*-mediate transformation. Plant Mol Biol 34: 913-922.

Wolters, A. -M. A., Trindade, L. M., Jacobsen, E. and Visser, R. G. F. 1998. Fluorescence in situ hybridization on extended DNA fibres as a tool to analyse complex T-DNA loci in potato. Plant J 13: 837-847.

Yanofsky, M. F., Porter, S. G., Young, C., Albright, L. M., Gordon, M. P. and Nester, E. W. 1986. The virD operon of *Agrobacterium tumefaciens* encodes a site-specific endonuclease. Cell 47: 471-477

Young, C. and Nester, E. W. 1988. Association of the virD2 protein with the 5' end of T strands in *Agrobacterium tumefaciens*. J Bacteriol 170: 3367-3374.

Yusibov, V. M., Steck, T. R., Gupta, V. and Gelvin, S. B. 1994. Association of single-stranded transferred DNA from *Agrobacterium tumefaciens* with tobacco cells. Proc Natl Acad Sci USA 91: 2994-2998.

Ziemienowicz, A., Gorlich, D., Lanka, E., Hohn, B., and Rossi, L. (1999). Import of DNA into mammalian nuclei by proteins originating from a plant pathogenic bacterium. Proc. Natl. Acad. Sci. U.S.A 96, 3729-3733.

Zupan, J. R. and Zambryski, P. 1995. Transfer of T-DNA from *Agrobacterium* to the plant cell. Plant Physiol 107: 1041-1047.

The invention claimed is:

1. A T-DNA transformation vector comprising T-DNA with flanking right and left T-DNA borders, wherein said right and left T-DNA borders are modified, wherein the modified right border comprises a single right border core sequence flanked by a right border outer region, and wherein the modified left T-DNA border comprises
   i) the inclusion of at least two left border core sequences separated by a sequence of at least 10-20 bp optionally carrying stop codons in three reading frames and in both directions, wherein the at least two left border core sequences are flanked only by a left border outer region; or
   ii) the inclusion of at least one integral nopaline-type left border region adjacent to and downstream or upstream of an integral octopine-type left border region.

2. The vector according to claim 1 wherein said modified left T-DNA border results in efficient nicking at the left border core repeat by the nicking complex at least involving the VirD1 and/or VirD2 proteins.

3. The T-DNA transformation vector according to claim 1 or 2, wherein the modifications of the T-DNA borders comprise the addition of recombination sites downstream of the left border core sequence and the addition of recombination sites upstream of the right border core sequence, said recombination sites being organized as repeats.

4. The vector according to claim 3 further comprising a second copy of a left border region upstream of and preferably adjacent to the single right border outer region and said recombination site upstream of the core sequence of said second left border region.

5. The vector according to claim 3 further comprising a recombinase gene located downstream of said recombination site downstream of said left border core sequence, and preferably, when present, adjacent to and downstream of the left border outer region.

6. The vector according to claim 5 comprising said recombinase gene flanked by repeats of recombination sites and said vector further comprising a second copy of a left border region located downstream of said recombinase gene flanked by said recombination sites.

7. The vector according to claim 6 further comprising additional recombination sites organized as repeats downstream of the second left border core sequence and upstream of the single right border core sequence.

8. The vector according to claim 3 characterized in that said recombination sites are located adjacent to and downstream and/or upstream of the left- and/or right border core sequences or are separated downstream and/or upstream from the left- and/or right border core sequences by a sequence of at least 10-20 bp in length optionally carrying stop codons in the three reading frames and in both directions.

9. The vector according to claim 3 wherein said recombination sites organized as repeats are defined as either site-specific recombination sites organized as direct repeats or as transposon border sequences organized as inverted repeats; and wherein said recombinase gene is defined as either a site-specific recombinase or a transposase gene, respectively.

10. A vector for *Agrobacterium*-mediated transformation, for agrolistic transformation or for gene therapy purposes comprising at least one modified T-DNA border as defined in claim 1 or 2, wherein said vector is chosen from binary transformation vectors, super-binary transformation vectors, co-integrate transformation vectors, Ri-derived transformation vectors and T-DNA carrying vectors used in agrolistic transformation or gene therapy.

11. A method for obtaining transgenic plants, yeasts, moulds or filamentous fungi comprising transforming a plant, yeast, mould or filamentous fungus with the transformation vector of claim 1 or 2 by *Agrobacterium*-mediated transformation.

12. A method for obtaining transgenic plants, yeasts, moulds or filamentous fungi comprising transforming a plant, yeast, mould or filamentous fungus with the transformation vector defined in claim 3 by *Agrobacterium*-mediated transformation in combination with a supply of a recombinase or transposase, for curing said resulting transformed cells from integrated vector backbone sequences possibly originating from said vector.

13. A method for obtaining transgenic plants, yeasts, moulds or filamentous fungi comprising transforming a plant, yeast, mould or filamentous fungus with the transformation vector defined in claim 5 for curing said resulting transformed cells from integrated vector backbone sequences possibly originating from said vector, optionally in combination with a supply of a recombinase or transposase.

14. A method for preventing the integration of vector backbone sequences in an *Agrobacterium*-mediated transformed cell comprising enhancing the efficiency of the nicking at the left border core sequence of a T-DNA vector, including vectors according to claim 1 or 2, by increasing the production of the VirD1 and/or VirD2 proteins comprised within the T-DNA nicking complex.

15. The method of claim 14 involving the integration of at least one additional copy of the virD locus into the genome or into an extrachromosomal entity of *Agrobacterium*.

16. The method of claim 15 wherein said additional copy of the virD locus is selected from the octopine-type virD locus or the nopaline-type virD locus.

17. The method according to claim 11 further comprising increasing the production of VirD1 and/or VirD2 proteins comprised within the T-DNA nicking complex.

18. A method of agrolistic-based transformation of a eukaryotic cell comprising transforming a eukaryotic cell with a T-DNA vector modified according to the alterations as defined in the vectors of claim 1 or 2.

19. A recombinant host cell comprising any of the vectors as defined in claim 1 or 2.

20. The host cell of claim 19 identified as being an *Agrobacterium tumefaciens*.

21. A transgenic plant cell or plant obtainable by an *Agrobacterium*-mediated transformation method according to claim 11, a part thereof, or progeny thereof.

22. A transgenic yeast, mould or filamentous fungus obtainable by an *Agrobacterium*-mediated transformation method according to claim 11.

23. A T-DNA transformation vector comprising T-DNA with flanking right and left T-DNA borders, wherein said right and left T-DNA borders are modified,
   wherein the modified right border comprises a single right border core sequence flanked by a right border outer region, and
   wherein the modified left T-DNA border comprises a single left border core sequence, wherein the single left border core sequence is further flanked by a natural left border outer region and an intra-T-DNA left border proximal region with a length of 10 to 100 bp, and which is enriched in the number of A- and T-residues, the percentage of AT-residues being 65 to 85%.

24. A method for obtaining transgenic plants or plant cells, yeasts, moulds or filamentous fungi comprising transforming a plant or plant cell, yeast, mould or filamentous fungus with the transformation vector of claim 23 by *Agrobacterium*-mediated transformation.

25. A recombinant host cell transformed with the vector of claim 23.

* * * * *

UNITED STATES PATENT AND TRADEMARK OFFICE
CERTIFICATE OF CORRECTION

| | | |
|---|---|---|
| PATENT NO. | : 7,749,751 B2 | Page 1 of 1 |
| APPLICATION NO. | : 10/168072 | |
| DATED | : July 6, 2010 | |
| INVENTOR(S) | : Anna Depicker et al. | |

It is certified that error appears in the above-identified patent and that said Letters Patent is hereby corrected as shown below:

Title page 1, left column, before "(51) Int. Cl.", insert

-- (30) Foreign Application Priority Data

Dec. 16, 1999    (EP) ........................ 99870264 --

Signed and Sealed this
First Day of March, 2011

David J. Kappos
*Director of the United States Patent and Trademark Office*

SEQUENCE LISTING

<160> NUMBER OF SEQ ID NOS: 10

<210> SEQ ID NO 1
<211> LENGTH: 44
<212> TYPE: DNA
<213> ORGANISM: Agrobacterium tumefaciens

<400> SEQUENCE: 1
tgatgctgac tggcaggata tataccgttg taatttgagc tcgt                    44

<210> SEQ ID NO 2
<211> LENGTH: 44
<212> TYPE: DNA
<213> ORGANISM: Agrobacterium tumefaciens

<400> SEQUENCE: 2
gcggcagcgg cggcaggata tattcaattg taaatggctt catg                    44

<210> SEQ ID NO 3
<211> LENGTH: 44
<212> TYPE: DNA
<213> ORGANISM: Agrobacterium tumefaciens

<400> SEQUENCE: 3
tatcagtgtt tgacaggata tattggcggg taaacctaag agaa                    44

<210> SEQ ID NO 4
<211> LENGTH: 44
<212> TYPE: DNA
<213> ORGANISM: Agrobacterium tumefaciens

<400> SEQUENCE: 4
ggctggctgg tggcaggata tattgtggtg taaacaaatt gacg                    44

<210> SEQ ID NO 5
<211> LENGTH: 74
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
catggagcgg cggcaggata tattcaattg taaatggcta gcggcggcag gatatattca    60
attgtaaatg gctg                                                     74

<210> SEQ ID NO 6
<211> LENGTH: 74
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gatccagcca tttacaattg aatatatcct gccgccgcta gccatttaca attgaatata    60
tcctgccgcc gctc                                                     74

<210> SEQ ID NO 7
<211> LENGTH: 106
<212> TYPE: DNA
<213> ORGANISM: Artificial Sequence

```
-continued

<220> FEATURE:
<223> OTHER INFORMATION: Description of Artificial Sequence:
      oligonucleotide

<400> SEQUENCE: 7
catggccggg aaatctacat ggatcagcaa tgagtatgat ggtcaatatg gagaaaaaga      60
aagagtaatt accaattttt tttcaattca aaaatgtaga tgtccg                   106

<210> SEQ ID NO 8
<211> LENGTH: 106
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gatccggaca tctacatttt tgaattgaaa aaaaattggt aattactctt tcttttctc      60 catattgacc atcatactca ttgctgatcc atgtagattt cccggc                    106

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ccggtggctc gagg                                                        14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tcgacctcga gcca                                                        14
```